(12) United States Patent
Nakamura et al.

(10) Patent No.: US 10,900,092 B2
(45) Date of Patent: Jan. 26, 2021

(54) CHLAMYDIA TRACHOMATIS DETECTING PRIMER SET, CHLAMYDIA TRACHOMATIS DETECTING METHOD USING SAME, AND REAGENT KIT THEREFOR

(71) Applicant: FUJIFILM WAKO PURE CHEMICAL CORPORATION, Osaka (JP)

(72) Inventors: Tatsuya Nakamura, Amagasaki (JP); Motoo Watanabe, Amagasaki (JP)

(73) Assignee: FUJIFILM WAKO PURE CHEMICAL CORPORATION, Osaka (JP)

( * ) Notice: Subject to any disclaimer, the term of this patent is extended or adjusted under 35 U.S.C. 154(b) by 126 days.

(21) Appl. No.: 16/088,711

(22) PCT Filed: Mar. 27, 2017

(86) PCT No.: PCT/JP2017/012348
§ 371 (c)(1),
(2) Date: Sep. 26, 2018

(87) PCT Pub. No.: WO2017/170376
PCT Pub. Date: Oct. 5, 2017

(65) Prior Publication Data
US 2019/0112638 A1    Apr. 18, 2019

(30) Foreign Application Priority Data
Mar. 30, 2016   (JP) .................... 2016-069163

(51) Int. Cl.
C12Q 1/689   (2018.01)
C12Q 1/68    (2018.01)
C12Q 1/6853  (2018.01)
C12Q 1/6869  (2018.01)

(52) U.S. Cl.
CPC ............ C12Q 1/689 (2013.01); C12Q 1/68 (2013.01); C12Q 1/6853 (2013.01); C12Q 1/6869 (2013.01); C12Q 2600/112 (2013.01)

(58) Field of Classification Search
CPC .................................................. C12Q 1/689
See application file for complete search history.

(56) References Cited

U.S. PATENT DOCUMENTS 9,458,513 B2    10/2016    Ishikawa et al.

FOREIGN PATENT DOCUMENTS

JP    5811086 B2    11/2015

OTHER PUBLICATIONS

Møller et al., "Comparison of Gen-Probe Transcription-Mediated Amplification, Abbott PCR, and Roche PCR Assays for Detection of Wild-Type and Mutant Plasmid Strains of *Chlamydia trachomatis* in Sweden," *J. Clin. Microbiol.*, 46(12): 3892-3895 (2008).
Japanese Patent Office, International Search Report in International Patent Application No. PCT/JP2017/012348 (dated Jun. 27, 2017).

*Primary Examiner* — Diana B Johannsen
(74) *Attorney, Agent, or Firm* — Leydig, Voit & Mayer, Ltd.

(57) ABSTRACT

The invention provides a primer set for detecting *Chlamydia trachomatis* containing (a) a first primer pair composed of a forward primer consisting of a base sequence represented by SEQ ID NO: 5 and (b) a reverse primer consisting of a base sequence represented by SEQ ID NO: 6, as well as a method for detecting *Chlamydia trachomatis* using the primer set, and a reagent kit therefor.

21 Claims, 5 Drawing Sheets
Specification includes a Sequence Listing.

SEQUENCE LISTING

<160> NUMBER OF SEQ ID NOS: 20

<210> SEQ ID NO 1
<211> LENGTH: 7492
<212> TYPE: DNA
<213> ORGANISM: Chlamydia trachomatis

<400> SEQUENCE: 1

```
tttgcaactc ttggtggtag actttgcaac tcttggtggt agactttgca atcttggtgg      60
tagactttgc aactcttggt ggtagacttg gtcataatgg acttttgtta aaaaatttct     120
taaaatctta gagctccgat tttgaatagc tttggttaag aaaatgggct cgatggcttt     180
```

-continued

```
ccataaaagt agattgttct taacttttgg ggacgcgtcg gaaatttggt tatctacttt    240
atctcatcta actagaaaaa attatgcgtc tgggattaac tttcttgttt ctttagagat    300
tctggattta tcggaaacct tgataaaggc tatttctctt gaccacagcg aatctttgtt    360
taaaatcaag tctctagatg ttttttaatgg aaaagtcgtt tcagaggcct ctaaacaggc    420
tagagcggca tgctacatat cttttcacaaa gttttttgtat agattgacca agggatatat    480
taaacccgct attccattga aagattttgg aaacactaca ttttttaaaa tccgagacaa    540
aatcaaaaca gaatcgattt ctaagcagga atggacagtt ttttttgaag cgctccggat    600
agtgaattat agagactatt taatcggtaa attgattgta caagggatcc gtaagttaga    660
cgaaattttg tctttgcgca cagacgatct atttttttgca tccaatcaga tttcctttcg    720
cattaaaaaa agacagaata aagaaaccaa aattctaatc acatttccta tcagcttaat    780
ggaagagttg caaaaataca cttgtgggag aaatgggaga gtatttgttt ctaaaatagg    840
gattcctgta acaacaagtc aggttgcgca taatttagg cttgcagagt tccatagtgc    900
tatgaaaata aaaattactc ccagagtact tcgtgcaagc gctttgattc atttaaagca    960
aataggatta aaagatgagg aaatcatgcg tatttcctgt ctctcatcga gacaaagtgt   1020
gtgttcttat tgttctgggg aagaggtaag tcctctagta caaacaccca caatattgtg   1080
atataattaa aattatattc atattctgtt gccagaaaaa acacctttag gctatattag   1140
agccatcttc tttgaagcgt tgtccttctcg agaggattta tcgtacgcaa atatcatctt   1200
tgcggttgcg tgtcccgtga ccttcattat gtcggagtct gagcacccta ggcgtttgta   1260
ctccgtcaca gcggttgctc gaagcacgtg cggggttatc ttaaaaggga ttgcagcttg   1320
tagtcctgct tgagagaacg tgcgggcgat ttgccttaac cccaccattt ttccggagcg   1380
agttacgaag acaaaacctc ttcgttgacc gatgtactct tgtagaaagt gcataaactt   1440
ctgaggataa gttataataa tcctcttttc tgtctgacgg ttcttaagct gggagaaaga   1500
aatggtagct tgttggaaac aaatctgact aatctccaag cttaagactt cagaggagcg   1560
tttacctcct tggagcattg tctgggcgat caaccaatcc cgggcgttga ttttttttag   1620
ctcttttagg aaggatgctg tttgcaaact gttcatcgca tccgttttta ctatttccct   1680
ggttttaaaa aatgttcgac tattttcttg tttagaaggt tgcgctatag cgactattcc   1740
ttgagtcatc ctgttaggga atcttgttaa ggaaatatag cttgctgctc gaacttgttt   1800
agtaccttcg gtccaagaag tcttggcaga ggaaactttt ttaatcgcat ctaggattag   1860
attatgattt aaaagggaaa actcttgcag attcatatcc aaagacaata gaccaatctt   1920
ttctaaagac aaaaaagatc ctcgatatga tctacaagta tgtttgttga gtgatgcggt   1980
ccaatgcata ataacttcga ataaggagaa gcttttcatg cgtttccaat aggattcttg   2040
gcgaattttt aaaacttcct gataagactt ttcgctatat tctaacgaca tttcttgctg   2100
caaagataaa atcccttac ccatgaaatc cctcgtgata taacctatcc gcaaaatgtc   2160
ctgattagtg aaataatcag gttgttaaca ggatagcacg ctcggtattt ttttatataa   2220
acatgaaaac tcgttccgaa atagaaaatc gcatgcaaga tatcgagtat cgttgttag    2280 gtaaagctct gatatttgaa gactctactg agtatattct gaggcagctt gctaattatg   2340
agtttaagtg ttcccatcat aaaaacatat tcatagtatt taaatactta aaagacaatg   2400
gattacctat aactgtagac tcggcttggg aagagctttt gcggcgtcgt atcaaagata   2460
tggacaaatc gtatctcggg ttaatgttgc atgatgcttt atcaaatgac aagcttagat   2520
ccgtttctca tacggttttc ctcgatgatt tgagcgtgtg tagcgctgaa gaaaatttga   2580
```

```
gcaatttcat tttccgctcg tttaatgagt acaatgaaaa tccattgcgt agatctccgt    2640
ttctattgct tgagcgtata aagggaaggc ttgatagtgc tatagcaaag acttttctta    2700
ttcgcagcgc tagaggccgg tctatttatg atatattctc acagtcagaa attggagtgc    2760
tggctcgtat aaaaaaaga cgagcagcgt tctctgagaa tcaaaattct ttctttgatg    2820
gcttcccaac aggatacaag gatattgatg ataaaggagt tatcttagct aaaggtaatt    2880
tcgtgattat agcagctagg ccatctatag ggaaaacagc tttagctata gacatggcga    2940
taaatcttgc ggttactcaa cagcgtagag ttggtttcct atctctagaa atgagcgcag    3000
gtcaaattgt tgagcggatt gttgctaatt aacaggaat atctggtgaa aaattacaaa    3060
gaggggatct ctctaaagaa gaattattcc gagtggaaga agctggagaa acagttagag    3120
aatcacattt ttatatctgc agtgatagtc agtataagct taatttaatc gcgaatcaga    3180
tccggttgct gagaaaagaa gatcgagtag acgtaatatt tatcgattac ttgcagttga    3240
tcaactcatc ggttggagaa aatcgtcaaa atgaaatagc agatatatct agaaccttaa    3300
gaggtttagc ctcagagcta acattccta tagtttgttt atcccaacta tctagaaaag    3360
ttgaggatag agcaaataaa gttcccatgc tttcagattt gcgagacagc ggtcaaatag    3420
agcaagacgc agatgtgatt tgtttatca ataggaagga atcgtcttct aattgtgaga    3480
taactgttgg gaaaaataga catggatcgg ttttctcttc ggtattacat ttcgatccaa    3540
aaattagtaa attctccgct attaaaaaag tatggtaaat tatagtaact gccacttcat    3600
caaaagtcct atccaccttg aaaatcagaa gtttggaaga agacctggtc aatctattaa    3660
gatatctccc aaaattggctc aaaatgggat ggtagaagtt ataggtcttg atttctcttc    3720
atctcattac catgcattag cagctatcca aagattactg accgcaacga attcaaggg    3780 gaacacaaaa ggggttgttt tatccagaga atcaaatagt tttcaatttg aaggatggat    3840
accaagaatc cgttttacaa aaactgaatt cttagaggct tatggagtta agcggtataa    3900
aacatccaga aataagtatg agtttagtgg aaaagaagct gaaactgctt tagaagcctt    3960
gtaccattta ggacatcaac cgttttaat agtggcaact agaactcgat ggactaatgg    4020
aacacaaata gtagaccgtt accaaactct ttctccgatc attaggattt acgaaggatg    4080
ggaaggttta actgacgaag aaaatataga tatagactta acaccttta attcaccatc    4140 tacacgaaaa cataaaggat tcgttgtaga gccatgtcct atcttggtag atcaaataga    4200
atcctacttt gtaatcaagc ctgcaaatgt ataccaagaa ataaaatgc gtttcccaaa    4260 cgcatcaaag tatgcttaca catttatcga ctgggtgatt acagcagctg cgaaaaagag    4320
acgaaaatta actaaggata attcttggcc agaaaacttg ttattaaacg ttaacgttaa    4380
aagtcttgca tatattttaa ggatgaatcg gtacatctgt acaaggaact ggaaaaaaat    4440
cgagttagct atcgataaat gtatagaaat cgccattcag cttggctggt tatctagaag    4500
aaaacgcatt gaatttctgg attcttctaa actctctaaa aaagaaattc tatatctaaa    4560
taaagagcgc tttgaagaaa taactaagaa atctaaagaa caaatggaac aagaatctat    4620
taattaatag caggcttgaa actaaaaacc taatttattt aaagctcaaa ataaaaagaa    4680
gttttaaaat gggaaattct ggttttttatt tgtataacac tgaaaactgc gtctttgctg    4740
ataatatcaa agttgggcaa atgacagagc cgctcaagga ccagcaaata atccttggga    4800
caaaatcaac acctgtcgca gccaaaatga cagcttctga tggaatatct ttaacagtct    4860
ccaataattc atcaaccaat gcttctatta caattggttt ggatgcggaa aaagcttacc    4920
```

-continued

```
agcttattct agaaaagttg ggaaatcaaa ttcttgatgg aattgctgat actattgttg    4980
atagtacagt ccaagatatt ttagacaaaa tcacaacaga cccttctcta ggtttgttga    5040
aagcttttaa caactttcca atcactaata aaattcaatg caacgggtta ttcactccca    5100
gtaacattga aactttatta ggaggaactg aaataggaaa attcacagtc acacccaaaa    5160
gctctgggag catgttctta gtctcagcag atattattgc atcaagaatg aaggcggcg    5220 ttgttctagc tttggtacga aaggtgatt ctaagccctg cgcgattagt tatggatact    5280
catcaggcgt tcctaattta tgtagtctaa gaaccagcat tactaataca ggattgactc    5340
caacaacgta ttcattacgt gtaggcggtt tagaaagcgg tgtggtatgg gttaatgccc    5400
tttctaatgg caatgatatt ttaggaataa caaatacttc taatgtatct tttttggaag    5460
taatacctca aacaaacgct taaacaattt ttattggatt tttcttatag gttttatatt    5520
tagagaaaac agttcgaatt acggggtttg ttatgcaaaa taaagaaaa gtgagggacg    5580 attttattaa aattgttaaa gatgtgaaaa aagatttccc cgaattagac ctaaaaatac    5640
gagtaaacaa ggaaaaagta actttcttaa attctccctt agaactctac cataaaagtg    5700
tctcactaat tctaggactg cttcaacaaa tagaaaactc tttaggatta ttcccagact    5760
ctcctgttct tgaaaaatta gaggataaca gtttaaagct aaaaaggct ttgattatgc    5820 ttatcttgtc tagaaaagac atgttttcca aggctgaata gacaacttac tctaacgttg    5880
gagttgattt gcacaccttta gttttttgct cttttaaggg aggaactgga aaacaacac    5940 tttctctaaa cgtgggatgc aacttggccc aattttagg gaaaaagtg ttacttgctg    6000 acctagaccc gcaatccaat ttatcttctg gattggggc tagtgtcaga ataaccaaa    6060 aaggcttgca cgacatagta tacaaatcaa acgatttaaa atcaatcatt gcgaaacaa    6120 aaaagatag tgtggaccta attcctgcat catttttatc cgaacagttt agagaattgg    6180
atattcatag aggacctagt aacaacttaa agttatttct gaatgagtac tgcgctcctt    6240
tttatgacat ctgcataata gacactccac ctagcctagg agggttaacg aaagaagctt    6300
ttgttgcagg agacaaatta attgcttgtt taactccaga acctttttct attctagggt    6360
tacaaaagat acgtgaattc ttaagttcgg tcggaaaacc tgaagaagaa cacattcttg    6420
gaatagcttt gtcttttttgg gatgatcgta actcgactaa ccaaatgtat atagacatta    6480
tcgagtctat ttacaaaaac aagctttttt caacaaaaat tcgtcgagat atttctctca    6540
gccgttctct tcttaaagaa gattctgtag ctaatgtcta tccaaattct agggccgcag    6600
aagatattct gaagttaacg catgaaatag caaatatttt gcatatcgaa tatgaacgag    6660
attactctca gaggacaacg tgaacaaact aaaaaaagaa gcggatgtct tttttaaaaa    6720
aaatcaaact gccgcttctc tagatttaa gaagacactt ccttccattg aactattctc    6780
agcaactttg aattctgagg aaagtcagag tttggatcga ttattttat cagagtccca    6840 aaactattcg gatgaagaat tttatcaaga agacatccta gcggtaaaac tgcttactgg    6900
tcagataaaa tccatacaga agcaacacgt acttctttta ggagaaaaaa tctataatgc    6960
tagaaaaatc ctgagtaagg atcacttctc ctcaacaact ttttcatctt ggatagagtt    7020
agtttttaga actaagtctt ctgcttacaa tgctcttgca tattcgagc ttttataaa    7080 cctccccaac caaactctac aaaaagagtt tcaatcgatc ccctataaat ccgcatatat    7140
tttggccgct agaaaaggcg atttaaaaac caaggtcgat gtgatagga agtatgtgg    7200 aatgtcgaac tcatcggcga taagggtgtt ggatcaattt cttccttcat ctagaaacaa    7260
agacgttaga gaaacgatag ataagtctga tttagagaag aatcgccaat tatctgattt    7320
```

```
cttaatagag atacttcgca tcatatgttc cggagtttct ttgtcctcct ataacgaaaa    7380
tcttctacaa cagcttttg aactttttaa gcaaaagagc tgatcctccg tcagctcata    7440
tatatattta ttatatatat atttatttag ggatttgatt ttacgagaga ga           7492
```

<210> SEQ ID NO 2
<211> LENGTH: 148
<212> TYPE: DNA
<213> ORGANISM: Chlamydia trachomatis

<400> SEQUENCE: 2

```
ccgctcaagg accagcaaat aatccttggg acaaaatcaa cacctgtcgc agccaaaatg    60
acagcttctg atggaatatc tttaacagtc tccataatt catcaaccaa tgcttctatt     120
acaattggtt tggatgcgga aaaagctt                                        148
```

<210> SEQ ID NO 3
<211> LENGTH: 173
<212> TYPE: DNA
<213> ORGANISM: Chlamydia trachomatis

<400> SEQUENCE: 3

```
cacagaattc cgtcgatcat aaggcttggt tcagcaggat tccccacagg cagagcttgc    60
aaggaggaag cagaactcaa agcggcaaat actaacaccg atttcaagag ttttttcatt    120
cttacctcta aattgtataa ttagctctct ttgtgctcgc tatcttttc tgg            173
```

<210> SEQ ID NO 4
<211> LENGTH: 174
<212> TYPE: DNA
<213> ORGANISM: Chlamydia trachomatis

<400> SEQUENCE: 4

```
cacagaattc cgtcgatcat aaggcttggt tcagcaggat tccccacagg cagagcttgc    60
aaggaggaag cagaactcaa agcggcaaat actaacaccg atttcaagag ttttttcatt    120
cttacctcta aattgtataa ttagctctct ttgtgctcgc tatcttttc tggc           174
```

<210> SEQ ID NO 5
<211> LENGTH: 24
<212> TYPE: DNA
<213> ORGANISM: Artificial Sequence
<220> FEATURE:
<223> OTHER INFORMATION: oligonucleotide primer

<400> SEQUENCE: 5

```
ccgctcaagg accagcaaat aatc                                            24
```

<210> SEQ ID NO 6
<211> LENGTH: 23
<212> TYPE: DNA
<213> ORGANISM: Artificial Sequence
<220> FEATURE:
<223> OTHER INFORMATION: oligonucleotide primer

<400> SEQUENCE: 6

```
aagcttttc cgcatccaaa cca                                              23
```

<210> SEQ ID NO 7
<211> LENGTH: 29
<212> TYPE: DNA
<213> ORGANISM: Artificial Sequence
<220> FEATURE:

<223> OTHER INFORMATION: oligonucleotide primer

<400> SEQUENCE: 7
ccagaaaaag atagcgagca caaagagag                29

<210> SEQ ID NO 8
<211> LENGTH: 28
<212> TYPE: DNA
<213> ORGANISM: Artificial Sequence
<220> FEATURE:
<223> OTHER INFORMATION: oligonucleotide primer

<400> SEQUENCE: 8
ccagaaaaag atagcgagca caaagaga                28

<210> SEQ ID NO 9
<211> LENGTH: 28
<212> TYPE: DNA
<213> ORGANISM: Artificial Sequence
<220> FEATURE:
<223> OTHER INFORMATION: oligonucleotide primer

<400> SEQUENCE: 9
gccagaaaaa gatagcgagc acaaagag                28

<210> SEQ ID NO 10
<211> LENGTH: 24
<212> TYPE: DNA
<213> ORGANISM: Artificial Sequence
<220> FEATURE:
<223> OTHER INFORMATION: oligonucleotide primer

<400> SEQUENCE: 10
cacagaattc cgtcgatcat aagg                24

<210> SEQ ID NO 11
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 11
cgctcaagga ccagcaaata                20

<210> SEQ ID NO 12
<211> LENGTH: 19
<212> TYPE: DNA
<213> ORGANISM: Artificial Sequence
<220> FEATURE:
<223> OTHER INFORMATION: oligonucleotide primer

<400> SEQUENCE: 12 gcttttccg catccaaac                19

<210> SEQ ID NO 13
<211> LENGTH: 18
<212> TYPE: DNA
<213> ORGANISM: Artificial Sequence
<220> FEATURE:
<223> OTHER INFORMATION: oligonucleotide primer

<400> SEQUENCE: 13
ccgctcaagg accagcaa                18

<210> SEQ ID NO 14
<211> LENGTH: 22
<212> TYPE: DNA
<213> ORGANISM: Artificial Sequence
<220> FEATURE:
<223> OTHER INFORMATION: oligonucleotide primer

<400> SEQUENCE: 14
agaagcattg gttgatgaat ta                                          22

<210> SEQ ID NO 15
<211> LENGTH: 22
<212> TYPE: DNA
<213> ORGANISM: Artificial Sequence
<220> FEATURE:
<223> OTHER INFORMATION: oligonucleotide primer

<400> SEQUENCE: 15
attgtgttga acaccgccc gg                                           22

<210> SEQ ID NO 16
<211> LENGTH: 24
<212> TYPE: DNA
<213> ORGANISM: Artificial Sequence
<220> FEATURE:
<223> OTHER INFORMATION: oligonucleotide primer

<400> SEQUENCE: 16
ttcggctcct tattcggttt gacc                                        24

<210> SEQ ID NO 17
<211> LENGTH: 24
<212> TYPE: DNA
<213> ORGANISM: Artificial Sequence
<220> FEATURE:
<223> OTHER INFORMATION: oligonucleotide primer

<400> SEQUENCE: 17
gatagcgagc acaaagagag ctaa                                        24

<210> SEQ ID NO 18
<211> LENGTH: 117
<212> TYPE: DNA
<213> ORGANISM: Chlamydia trachomatis

<400> SEQUENCE: 18
ccgctcaagg accagcaaat aatccttggg acaaaatcaa cacctgtcgc agccaaaatg    60
acagcttctg atggaatatc tttaacagtc tccaataatt catcaaccaa tgcttct     117

<210> SEQ ID NO 19
<211> LENGTH: 145
<212> TYPE: DNA
<213> ORGANISM: Chlamydia trachomatis

<400> SEQUENCE: 19
cgctcaagga ccagcaaata atccttggga caaaatcaac acctgtcgca gccaaaatga    60
cagcttctga tggaatatct ttaacagtct ccaataattc atcaaccaat gcttctatta   120
caattggttt ggatgcggaa aaagc                                        145

<210> SEQ ID NO 20
<211> LENGTH: 164
<212> TYPE: DNA
<213> ORGANISM: Chlamydia trachomatis

```
<400> SEQUENCE: 20
cacagaattc cgtcgatcat aaggcttggt tcagcaggat tccccacagg cagagcttgc      60
aaggaggaag cagaactcaa agcggcaaat actaacaccg atttcaagag tttttttcatt    120 cttacctcta aattgtataa ttagctctct ttgtgctcgc tatc                      164
```

CHLAMYDIA TRACHOMATIS DETECTING PRIMER SET, CHLAMYDIA TRACHOMATIS DETECTING METHOD USING SAME, AND REAGENT KIT THEREFOR

CROSS-REFERENCE TO RELATED APPLICATIONS

This patent application is the U.S. national phase of International Patent Application No. PCT/JP2017/012348, filed Mar. 27, 2017, which claims the benefit of Japanese Patent Application No. 2016-069163, filed on Mar. 30, 2016, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 14,536 bytes ASCII (Text) file named "740448Sequence-Listing.txt," created Sep. 7, 2018.

TECHNICAL FIELD

The present invention relates to a primer set for detecting *Chlamydia trachomatis* (hereinafter, abbreviated to CT in some cases), a method for detecting *Chlamydia trachomatis* using the same, and a reagent kit for performing the method.

BACKGROUND ART

Recently, as the sexual culture has become diverse, and the pattern of sexual behavior has changed mainly by the young people, *Chlamydia* infections have markedly increased.

The bacterium causing the *Chlamydia* infections is *Chlamydia trachomatis* which infects the eye, the urethra, the cervix, or the pharynx of human beings and causes various inflammations. In addition, there are about 15 serotypes (A-K, Ba, L1-L3, and the like) of *Chlamydia trachomatis* that are known to be able to infect human beings. Therefore, a plurality of serotypes of *Chlamydia trachomatis* needs to be detected.

Currently, as a method for detecting *Chlamydia trachomatis*, a method of detecting a cryptic plasmid specific to *Chlamydia trachomatis* by using a nucleic acid amplification reaction is mainly used (Patent Literature 1 and Non-Patent Literature 1).

In addition, it is recommended that clinical samples of *Chlamydia trachomatis* are collected from urine, the pharynx and the cervix. However, it is known that the samples derived from urine, the pharynx, and the cervix contain human genomic DNA, and the human genomic DNA inhibits a target nucleic acid amplification reaction. Accordingly, it is necessary to specifically amplify *Chlamydia trachomatis* even in the presence of the human genomic DNA.

CITATION LIST

Patent Literature

[Patent Literature 1] JP5811086B

Non-Patent Literature

[Non-Patent Literature 1] Moller, J. K., et al., Journal of Clinical Microbiology, 2008, 46, p. 3892-3895

SUMMARY OF INVENTION

Technical Problem

However, with the detection methods disclosed in Patent Literature 1 and Non-Patent Literature 1, in a case where a nucleic acid amplification reaction is performed in the presence of foreign DNA such as human genomic DNA, a large number of nonspecific nucleic acids are amplified. As a result, in a case where *Chlamydia trachomatis* is detected using samples derived from urine, the pharynx, and the cervix, sometimes a false positive occurs.

In addition, with the detection method disclosed in Non-Patent Literature 1, it is impossible to detect a plurality of serotypes of *Chlamydia trachomatis*, and accordingly, sometimes a false negative occurs.

That is, with the method for detecting *Chlamydia trachomatis* of the related art in which a nucleic acid amplification reaction is used, unfortunately, a misdiagnosis such as a false positive or a false negative is made.

The present invention has been made in consideration of the circumstances described above, and an object thereof is to provide a primer set for detecting *Chlamydia trachomatis* which has a low probability of making a misdiagnosis such as a false negative or a false positive and has excellent sensitivity and specificity.

Solution to Problem

The present invention has been made to achieve the object and is constituted as below.

(1) A primer set for detecting *Chlamydia trachomatis* comprising a first primer pair composed of a combination of a forward primer consisting of a base sequence represented by SEQ ID NO: 5 and a reverse primer consisting of a base sequence represented by SEQ ID NO: 6.

(2) A method for detecting *Chlamydia trachomatis* comprising performing a nucleic acid amplification reaction by using the primer set described in (1) and using a nucleic acid in a sample as a template and detecting a nucleic acid amplification product obtained.

(3) A reagent kit for detecting *Chlamydia trachomatis* comprising the primer set described in (1).

Advantageous Effects of Invention

According to the primer set for detecting *Chlamydia trachomatis* of the present invention, even in the presence of foreign DNA such as human genomic DNA, the amplification of nonspecific nucleic acids can be suppressed. In addition, a plurality of serotypes of *Chlamydia trachomatis* that can infect human beings can be detected.

Furthermore, the method of the present invention, in which the primer set for detecting *Chlamydia trachomatis* of the present invention is used, makes it possible to reduce misdiagnoses such as a false negative or a false positive

DESCRIPTION OF EMBODIMENTS

Figure 1:
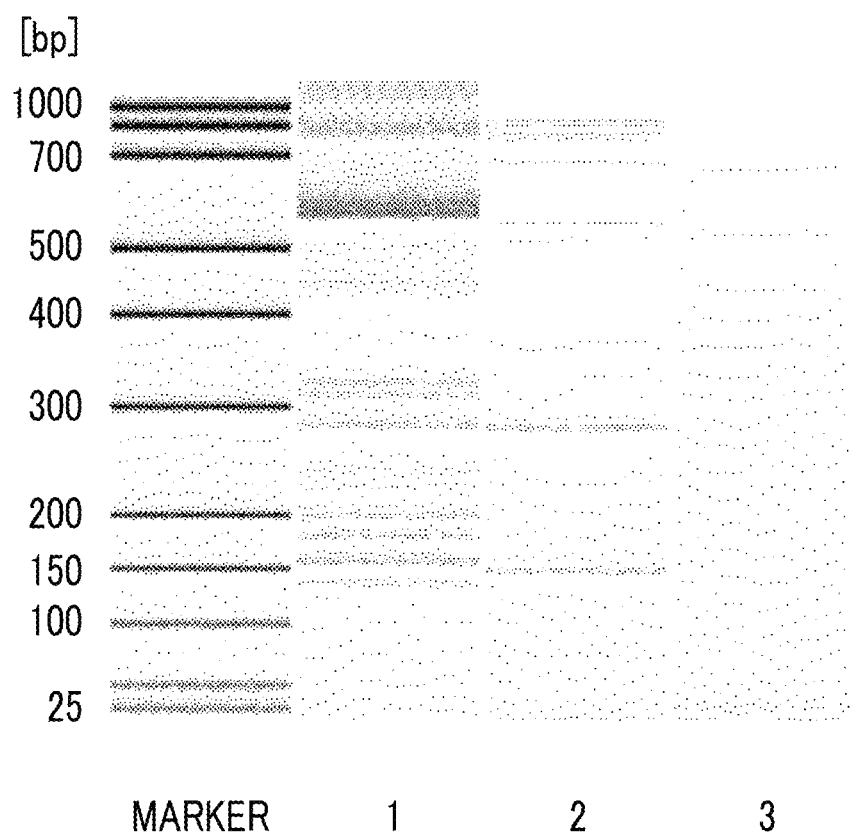
FIG. 1 is a phoretic diagram obtained by separating and detecting PCR amplification products, which are obtained in Example 2 and Comparative Examples 1 and 2 from human genomic DNA-containing samples by using various primer pairs, by capillary electrophoresis.

<1> Primer Set for Detecting *Chlamydia trachomatis* of the Present Invention

The primer set for detecting *Chlamydia trachomatis* of the present invention (hereinafter, simply described as a primer set of the present invention in some cases) contains a first primer pair (hereinafter, simply described as a first primer pair according to the present invention in some cases) composed of a combination of a forward primer consisting of a base sequence represented by SEQ ID NO: 5 and a reverse primer consisting of a base sequence represented by SEQ ID NO: 6.

The forward primer consisting of a base sequence represented by SEQ ID NO: 5 and the reverse primer consisting of a base sequence represented by SEQ ID NO: 6 are annealed to a cryptic plasmid pLGV440 of *Chlamydia trachomatis* (hereinafter, simply described as a cryptic plasmid in some cases). In a case where a nucleic acid amplification reaction (PCR or the like) is performed using the first primer pair of the present invention composed of the combination of these primers and a complete base sequence of the cryptic plasmid (SEQ ID NO: 1, GenBankID: HE603230.1, $1^{st}$ to $7,492^{nd}$ bases), in the complete base sequence of the cryptic plasmid, a domain of the $4,770^{th}$ to $4,917^{th}$ bases (148 base pairs) having a base sequence represented by SEQ ID NO: 2 is amplified.

The primer set of the present invention may further contain, in addition to the first primer pair according to the present invention, a second primer pair (hereinafter, simply described as a second primer pair according to the present invention in some cases) composed of a combination of a forward primer and a reverse primer annealed with genomic DNA of *Chlamydia trachomatis* (hereinafter, simply described as CT genomic DNA in some cases).

The second primer pair according to the present invention is not limited as long as it is annealed with the CT genomic DNA. It should be noted that the complete base sequence of the CT genomic DNA is disclosed in GenBankID: HE601796.2.

In addition, the second primer pair according to the present invention is a base sequence different from the first primer pair according to the present invention.

The second primer pair according to the present invention may be designed according to a known method.

For example, the primers may be designed using primer design software (for instance, Primer3 or the like) which is generally used for designing primers.

At this time, the number of bases of each of the forward primer and the reverse primer in the second primer pair according to the present invention is 10 to 50 which is considered as the number of bases necessary for maintaining the specificity of a general primer sequence. The number of bases is preferably 10 to 35, more preferably 15 to 35, and particularly preferably 18 to 30.

Specific examples of the second primer pair according to the present invention include a primer pair composed of a combination of a forward primer consisting of a base sequence represented by any of SEQ ID NOS: 7 to 9 and a reverse primer consisting of a base sequence represented by SEQ ID NO: 10.

In a case where a nucleic acid amplification reaction (PCR or the like) is performed using, as the second primer pair according to the present invention, a forward primer consisting of a base sequence represented by SEQ ID NO: 7 and a reverse primer consisting of a base sequence represented by SEQ ID NO: 10, in the complete base sequence of the CT genomic DNA, a domain of $782,264^{th}$ to $782,436^{th}$ bases (SEQ ID NO: 3: 173 base pairs) is amplified.

In addition, in a case where a nucleic acid amplification reaction (PCR or the like) is performed using a forward primer consisting of a base sequence represented by SEQ ID NO: 8 and a reverse primer consisting of a base sequence represented by SEQ ID NO: 10, in the complete base sequence of the CT genomic DNA, a domain of the $782,264^{th}$ to $782,436^{th}$ bases (SEQ ID NO: 3: 173 base pairs) is amplified.

Furthermore, in a case where a nucleic acid amplification reaction (PCR or the like) is performed using a forward primer consisting of a base sequence represented by SEQ ID NO: 9 and a reverse primer consisting of a base sequence represented by SEQ ID NO: 10, in the complete base sequence of the CT genomic DNA, a domain of the $782,264^{th}$ to $782,437^{th}$ bases (SEQ ID NO: 4: 174 base pairs) is amplified.

Among the above, as the second primer pair according to the present invention, a primer pair composed of a combination of a forward primer consisting of a base sequence represented by SEQ ID NO: 7 or 8 and a reverse primer consisting of a base sequence represented by SEQ ID NO: 10 is preferable, and a primer pair composed of a combination of a forward primer consisting of a base sequence represented by SEQ ID NO: 7 and a reverse primer consisting of a base sequence represented by SEQ ID NO: 10 is more preferable.

In a case where the primer set of the present invention, which is obtained by adding the second primer pair according to the present invention that is targeted to the CT genomic DNA to the first primer pair according to the present invention that is targeted to the cryptic plasmid, is used, even a cryptic plasmid-deficient *Chlamydia trachomatis* mutant (An. Q., et al., Journal of Clinical Microbiology, 1992, 30, p. 2814-2821) which has been reported recently can be detected by amplifying the nucleic acid thereof.

The method for obtaining the primers (hereinafter, simply described as primers according to the present invention in some cases) constituting the first primer pair according to the present invention and the second primer pair according to the present invention is not particularly limited. Examples of the method include a method of preparing the primers by a known chemical synthesis method and a method of obtaining the primers by a genetic engineering method in which a vector or the like is used. Among these, the chemical synthesis method is preferable because this method makes it possible to easily obtain a large amount of primers of certain quality at low costs.

For example, in a case where oligonucleotides are synthesized by a general phosphoramidite method by using a DNA synthesizer and purifying DNA by anion column chromatography, target primers according to the present invention can be obtained.

It should be noted that the primers according to the present invention may be purchased from an entrusted manufacturer performing primer synthesis.

At least one of the primers according to the present invention may be labeled with a labeling substance.

In a case where the primers according to the present invention labeled with a labeling substance are used, and only the first primer pair according to the present invention is used, at least either the forward primer or the reverse primer may be labeled with the labeling substance.

In addition, in a case where the primers according to the present invention labeled with a labeling substance are used, and two primer pairs constituted with the first primer pair according to the present invention and the second primer pair according to the present invention are used, at least either the forward primer or the reverse primer of the first primer pair according to the present invention and at least either the forward primer or the reverse primer of the second primer pair according to the present invention may be labeled with the labeling substance.

Examples of the labeling substance used for labeling the primers according to the present invention with a labeling substance include known labeling substances such as a fluorescent substance, a radioisotope, an enzyme, and a luminescent substance. Among these, the fluorescent substance is preferable.

Examples of the fluorescent substance include TAMRA™ (manufactured by Sigma-Aldrich Co. LLC.), Alexa555 and Alexa647 (manufactured by Thermo Fisher Scientific Inc.), Cy3 and Cy5 based on a cyanine dye (manufactured by GE Healthcare), fluorescein, and the like. Among these, TAMRA™ (manufactured by Sigma-Aldrich Co. LLC.) is preferable.

Examples of the radioisotope include $^{32}P$, $^{33}P$, $^{35}S$, and the like.

Examples of the enzyme include alkaline phosphatase, horseradish peroxidase, and the like.

Examples of the luminescent substance include chemiluminescent reagents containing acridinium ester, and the like.

It should be noted that in the primers according to the present invention labeled with a labeling substance, the labeling substance may be bonded to the primers directly or through a linker. The linker may be a linker generally used in the field of the related art or a nucleic acid constituted with 1 to 3 bases.

Examples of the method for labeling the primers according to the present invention with a labeling substance include an oligonucleotide labeling method which is generally performed in the field of the related art, and the method may be appropriately selected for each labeling substance.

Examples of the method for labeling the primers according to the present invention with a fluorescent substance include a method of incorporating a fluorescein-labeled nucleotide into the primers according to a known method.

In addition, by a method of replacing oligonucleotides in a sequence with a nucleotide having a linker arm (Nucleic Acids Res., 1986, Vol. 14, p. 6115), the nucleotide can also be labeled with a fluorescent substance. For example, there is a method in which uridine having a linker arm in 5-position is chemically synthesized from deoxyuridine by the synthesis method disclosed in JP1985-500717A (JP-S60-500717A), oligonucleotides containing the deoxyuridine are synthesized, and then a fluorescent substance is introduced into the oligonucleotide chain (JP1985-500717A (JP-S60-500717A)).

Examples of the method for labeling the primers according to the present invention with a radioisotope include a method of labeling the primers by incorporating a radioisotope-labeled nucleotide into the primers at the time of synthesizing the primers, a method of labeling the primers with a radioisotope after the primers are synthesized, and the like. Specifically, examples thereof include a generally used random primer method, Nick translation, a 5'-terminal labeling method by using T4 polynucleotide kinase, a 3'-terminal labeling method by using terminal deoxynucleotidyl transferase, and the like.

Examples of the method for labeling the primers according to the present invention with an enzyme include a direct labeling method in which molecules of an enzyme such as alkaline phosphatase or horseradish peroxidase are directly bonded to the primers to be labeled through a covalent bond.

Examples of the method for labeling the primers according to the present invention with a luminescent substance include a method of labeling a nucleotide with a luminescent substance according to a known method.

In addition, the labeling substance may be bonded to the primers according to the present invention by a detection system in which a biotin-avidin reaction is used.

At this time, labeling may be performed according to the technique described in E. P. Diamandis, T. K. Christopoulos, Clinical Chemistry 1991, 37, p.p. 625-636.

<2> Method for Detecting *Chlamydia Trachomatis* of the Present Invention

The method for detecting *Chlamydia trachomatis* of the present invention (hereinafter, simply described as a CT detecting method of the present invention in some cases) contains performing a nucleic acid amplification reaction by using a primer set; which contains a first primer pair composed of a combination of a forward primer consisting of a base sequence represented by SEQ ID NO: 5 and a reverse primer consisting of a base sequence represented by SEQ ID NO: 6, and using a nucleic acid in a sample as a template and detecting a nucleic acid amplification product obtained.

Examples of the sample used in the CT detecting method of the present invention include various clinical samples such as urine, a urethral swab suspension, a vaginal swab suspension, a cervical swab suspension, a gargle, an oral cavity swab suspension, and a pharyngeal swab suspension; cultured bacteria, and the like. Before CT detection of the present invention, these samples may be pretreated by the operations such as the concentration and separation of bacteria present in the samples or the extraction and purification of DNA from the bacteria. As the pretreatment method, the samples may be treated with an enzyme, a surfactant, an alkali, heat, or the like.

The extraction and purification of DNA from the samples may be performed according to a known method. Specifically, the extraction and purification of DNA may be performed after the cell wall of *Chlamydia* is disrupted.

Examples of the method for disrupting the cell wall of *Chlamydia* in the samples include a method of disrupting the membrane structure of *Chlamydia* by treating the bacteria with a surfactant such as SDS or with a protein denaturant such as guanidine thiocyanate (GTC), a method of physically cracking the cell wall by using glass beads, and the like.

The extraction and purification of DNA may be performed by a method of disrupting the cell wall of *Chlamydia* and then extracting and purifying DNA by using phenol and chloroform, a method of extracting and purifying DNA by using ethanol, isopropanol, and the like.

In addition, the extraction and purification of DNA may be performed using a commercial kit [for example, Genomic-tip (manufactured by QIAGEN)].

In the CT detecting method of the present invention, the second primer pair according to the present invention may also be used. Specifically, the CT detecting method is carried out by performing a nucleic acid amplification reaction by using a primer set, which contains a first primer pair composed of a combination of a forward primer consisting of a base sequence represented by SEQ ID NO: 5 and a reverse primer consisting of a base sequence represented by SEQ ID NO: 6 and a second primer pair composed of a combination of a forward primer consisting of a base sequence represented by any of SEQ ID NOS: 7 to 9 and a reverse primer consisting of a base sequence represented by SEQ ID NO: 10, and using a nucleic acid in a sample as a template, and detecting a nucleic acid amplification product obtained.

In a case where the first primer pair and the second primer pair according to the present invention are used in the CT detecting method of the present invention, as the combination of the first primer pair and the second primer pair according to the present invention, (1) or (2) shown in the following Table 1 is preferable, and (1) is more preferable.

TABLE 1

|  | First primer pair | Second primer pair |
| --- | --- | --- |
| (1) | Forward primer SEQ ID NO: 5<br>Reverse primer SEQ ID NO: 6 | Forward primer SEQ ID NO: 7<br>Reverse primer SEQ ID NO: 10 |
| (2) | Forward primer SEQ ID NO: 5<br>Reverse primer SEQ ID NO: 6 | Forward primer SEQ ID NO: 8<br>Reverse primer SEQ ID NO: 10 |

In the CT detecting method of the present invention, as at least one of the primers according to the present invention, a primer labeled with a labeling substance may be used.

In the CT detecting method of the present invention, in a case where the primer according to the present invention that is labeled with a labeling substance is used, and only the first primer pair according to the present invention is used as CT detecting primers, at least either the forward primer or the reverse primer may be labeled with a labeling substance.

In the CT detecting method of the present invention, in a case where the primers according to the present invention that are labeled with a labeling substance are used, and two primer pairs including the first primer pair according to the present invention and the second primer pair according to the present invention are used as primers for detecting CT, at least either the forward primer or the reverse primer of the first primer pair according to the present invention and at least either the forward primer or the reverse primer of the second primer pair according to the present invention may be labeled with a labeling substance.

Although *Neisseria gonorrhoeae* and *Chlamydia trachomatis* simultaneously cause infection in many cases, a cure for *Neisseria gonorrhoeae* is different from that for *Chlamydia trachomatis*. Accordingly, simultaneous detection of *Chlamydia trachomatis* and *Neisseria gonorrhoeae* has a great significance. Therefore, for simultaneously detecting *Chlamydia trachomatis* and *Neisseria gonorrhoeae*, a nucleic acid amplification reaction may be performed using the primer set of the present invention and a primer pair detecting *Neisseria gonorrhoeae* such that a nucleic acid amplification product derived from *Chlamydia trachomatis* and a nucleic acid amplification product derived from *Neisseria gonorrhoeae* are detected.

Furthermore, appropriate bacteria may be selected as an internal control, a nucleic acid derived from the bacteria and a primer pair for detecting the bacteria may be additionally used, a nucleic acid amplification reaction may be performed using the primer set of the present invention, and a nucleic acid amplification product derived from *Chlamydia trachomatis* and a nucleic acid amplification product derived from the bacteria may be detected so as to confirm whether or not the nucleic acid amplification reaction was correctly performed.

It should be noted that, for example, in a case where only *Chlamydia trachomatis* is detected, the bacteria selected as an internal control are bacteria other than *Chlamydia trachomatis*, and in a case where *Chlamydia trachomatis* and *Neisseria gonorrhoeae* are detected, the bacteria selected as an internal control are bacteria other than *Chlamydia trachomatis* and *Neisseria gonorrhoeae*.

It should be noted that in the CT detecting method of the present invention, as each of the primers constituting the primer pair for detecting *Neisseria gonorrhoeae* and the primer pair for detecting the internal control, those labeled with a labeling substance may be used.

In the CT detecting method of the present invention, in a case where the primer pair for detecting *Neisseria gonorrhoeae* that is labeled with a labeling substance is used, at least either the forward primer or the reverse primer of the primer pair for detecting *Neisseria gonorrhoeae* may be labeled with a labeling substance.

In the CT detecting method of the present invention, in a case where the primer pair for detecting the internal control that is labeled with a labeling substance is used, at least either the forward primer or the reverse primer of the primer pair for detecting the internal control may be labeled with a labeling substance.

In the CT detecting method of the present invention, in a case where the primer pair for detecting *Neisseria gonorrhoeae* and the primer pair for detecting the internal control that are labeled with a labeling substance are used, at least either the forward primer or the reverse primer of the primer pair for detecting *Neisseria gonorrhoeae* and at least either the forward primer or the reverse primer of the primer pair for detecting the internal control may be labeled with a labeling substance.

The details of the primers, the primer pairs, the primer set, the labeling substance, and the labeling method using the labeling substance used in the CT detecting method of the present invention are as described in <1> primer set for detecting *Chlamydia trachomatis* of the present invention.

The nucleic acid amplification reaction (hereinafter, simply described as a nucleic acid amplification reaction according to the present invention in some cases) performed in the CT detecting method of the present invention by using the primer set of the present invention is not particularly limited, and may be carried out according to a known method. Specifically, examples of the method include a Polymerase Chain Reaction (PCR) method, a Transcription-mediated amplification (TMA) method, a Strand Displacement Amplification (SDA) method, and the like. Among these, the PCR method is preferable.

The target of the nucleic acid amplification reaction according to the present invention is generally DNA. However, even in a case where the target is RNA, complementary DNA (cDNA) can be used as a target by being synthesized through reverse transcription. Examples of the method include a Transcription-Reverse Transcription Concerted Reaction (TRC) method and the like.

A nucleic acid synthase such as a TaqDNA polymerase [for example, KOD Exo(-) (manufactured by Toyobo Co., Ltd)] or a nucleic acid synthesis substrate such as dNTP (dATP, dCTP, dGTP, or dGTTP) used in the nucleic acid amplification reaction according to the present invention may be those generally used in the field of the related art.

Furthermore, a reaction solution in the nucleic acid amplification reaction according to the present invention may contain a buffer such as Tris-HCl or $K_2HPO_4$, a salt such as $MgCl_2$, KCl, or $(NH_4)_2SO_4$, a surfactant such as polyethylene glycol, Triton (manufactured by The Dow Chemical Company), Nonidet (manufactured by Shell Chemicals), or CHAPS (manufactured by DOJINDO Laboratories Co., Ltd.), a preservative such as ProClin 300 (manufactured by Sigma-Aldrich Co. LLC.), and a polypeptide such as bovine serum albumin (BSA). In addition to the above components, the reaction solution may contain other optional components as long as the nucleic acid amplification reaction is not inhibited.

In the CT detecting method of the present invention, the amplification product may be detected based on a known method that is generally performed in the field of the related art. Specifically, examples of the method include (a) detection method by electrophoresis, (b) detection method by a real-time method, and the like. Among these, (a) detection method by electrophoresis is preferable.

Hereinafter, each of the methods will described.

(a) Detection Method by Electrophoresis

The detection method by electrophoresis is a technique of separating and detecting the amplification product, which is obtained by the nucleic acid amplification reaction according to the present invention by using the primer pair according to the present invention, by electrophoresis. Specific examples of the method include (a-1) labeled primer method, (a-2) intercalator method, and (a-3) labeled probe method.

(a-1) Labeled Primer Method

The labeled primer method is a method in which "by using a primer pair containing a labeled primer, which is obtained by labeling at least one of the primers according to the present invention with a labeling substance, and using a nucleic acid in a test sample as a template, the nucleic acid amplification reaction according to the present invention is performed. Then, the obtained amplification product is separated by electrophoresis, and the label in the amplification product is detected. As a result, in a case where the label of the amplification product can be detected as the number of base pairs of the product amplified by the primer pair according to the present invention, it is determined that 'the test sample is positive for *Chlamydia trachomatis*'".

It should be noted that in the present specification, "detecting a label" means that a labeling substance is directly or indirectly measured based on the properties of the labeling sub stance.

The details of the primers, the primer pair, the labeling substance, and the labeling method using a labeling substance in the labeled primer method are as described in <1> primer set for detecting *Chlamydia trachomatis* of the present invention.

The electrophoresis in the labeled primer method may be based on a method in which substances migrate at different speeds or migrate different distances depending on the charge intensity of the substances. Specifically, examples of the electrophoresis include capillary electrophoresis, agarose gel electrophoresis, polyacrylamide gel electrophoresis (slab electrophoresis), starch gel electrophoresis, isoelectric focusing, and the like. Among these, the agarose gel electrophoresis and the capillary electrophoresis are preferable, and the capillary electrophoresis is more preferable.

It should be noted that in a case where the capillary electrophoresis is performed, it may be performed according to known methods described in WO2007/027495, WO2011/118496, WO2008/075520, and the like.

Hereinbelow, the labeled primer method will be specifically described for (a-1-1) Case where first primer pair according to the present invention is used and (a-1-2) Case where first primer pair according to the present invention and second primer pair according to the present invention are used.

(a-1-1) Case where First Primer Pair According to the Present Invention is Used

For example, first, at least one of the primers in the first primer pair according to the present invention is labeled with a labeling substance. Then, by using the first primer pair according to the present invention containing the primer labeled with the labeling substance and using a nucleic acid in a sample as a template, the nucleic acid amplification reaction according to the present invention is performed. Thereafter, the amplification product obtained is separated by electrophoresis, and the label in the amplification product is detected.

As a result, in a case where the label of the amplification product can be detected as the number of base pairs of the product amplified by the first primer pair according to the present invention, it is determined that "the test sample is positive for *Chlamydia trachomatis*".

(a-1-2) Case where First Primer Pair According to the Present Invention and Second Primer Pair According to the Present Invention are Used For example, first, at least one of the primers in the first primer pair according to the present invention and at least one of the primers in the second primer pair according to the present invention are labeled with a labeling substance. Then, by using the first primer pair according to the present invention labeled with the labeling substance and the second primer pair according to the present invention that contains a primer labeled with a labeling substance and using a nucleic acid in a sample as a template, the nucleic acid amplification reaction according to the present invention is performed. Thereafter, an amplification product (first amplification product) obtained by the nucleic acid amplification reaction according to the present invention by using the first primer pair according to the present invention and an amplification product (second amplification product)

obtained by the nucleic acid amplification reaction according to the present invention by using the second primer pair according to the present invention are separated respectively by electrophoresis, and the labels in the first amplification product and the second amplification product are detected.

As a result, in a case where at least either a case where the label of the first amplification product can be detected as the number of base pairs of the product amplified by the first primer pair according to the present invention or a case where the label of the second amplification product can be detected as the number of base pairs of the product amplified by the second primer pair according to the present invention is shown, it is determined that "the test sample is positive for *Chlamydia trachomatis*".

It should be noted that specific examples of the second primer pair according to the present invention include primer pairs composed of a combination of a forward primer consisting of a base sequence represented by any of SEQ ID NOS: 7 to 9 and a reverse primer consisting of a base sequence represented by SEQ ID NO: 10. Among these, a primer pair composed of a combination of a forward primer consisting of a base sequence represented by SEQ ID NO: 7 or 8 and a reverse primer consisting of a base sequence represented by SEQ ID NO: 10 is preferable, and a primer pair composed of a combination of a forward primer consisting of a base sequence represented by SEQ ID NO: 7 and a reverse primer consisting of a base sequence represented by SEQ ID NO: 10 is more preferable.

In a case where *Neisseria gonorrhoeae* or microbes such as bacteria selected as an internal control are detected at the same time, a nucleic acid amplification reaction and the detection method may be performed in the same manner as that described above by using a primer pair labeled with a labeling substance for detecting *Neisseria gonorrhoeae* or microbes such as bacteria selected as an internal control in addition to the primer pair according to the present invention that is for detecting *Chlamydia trachomatis*.

(a-2) Intercalator Method

The intercalator method is a method in which "by using the primer pair according to the present invention and using a nucleic acid in a test sample as a template, the nucleic acid amplification reaction according to the present invention is performed, and the amplification product obtained is separated by electrophoresis. Then, the amplification product is stained with an intercalator, and the fluorescence derived from the intercalator is detected. As a result, in a case where the fluorescence derived from the intercalator can be detected, it is determined that 'the test sample is positive for *Chlamydia trachomatis*'".

The details of the primer pair in the intercalator method are as described in <1> primer set for detecting *Chlamydia trachomatis* of the present invention.

Examples of the electrophoresis in the intercalator method include the same ones as those exemplified above for (a-1) labeled primer method, and preferable ones are also the same as those described above.

In addition, as the intercalator in the intercalator method, any intercalator that is generally used in the field of the related art may be adopted. Specific examples thereof include intercalators in the following (1) to (5) and intercalator analogues in the following (6) and (7).

That is, examples of the intercalator include (1) ethidium compound [for example, ethidium bromide, an ethidium homodimer 1 (EthD-1), an ethidium homodimer 2 (EthD-2), ethidium monoazide bromide (EMA), dihydroethidium; and the like].

(2) acridine dye (for example, acridine orange and the like), (3) iodine compound (propidium iodide, hexidium iodide, and the like) and cyanine dimer-based dye [for example, POPO-1, BOBO-1, YOYO-1, TOTO-1, POPO-3, LOLO-1, BOBO-3, YOYO-3, TOTO-3 (all manufactured by Thermo Fisher Scientific Inc.), and the like], (4) cyanine monomer-based dye [for example, PO-PRO-1, BO-PRO-1, YO-PRO-1, TO-PRO-1, JO-PRO-1, PO-PRO-3, LO-PRO-1, BO-PRO-3, YO-PRO-3, TO-PRO-3, TO-PRO-5 (all manufactured by Thermo Fisher Scientific Inc.), and the like], (5) SYTOX-based dye [for example, SYTOX Green, SYTOX Blue, SYTOX Orange (all manufactured by Thermo Fisher Scientific and the like], SYBR-based dye [for example, SYBR Gold, SYBR Green I, and SYBR Green II (all manufactured by Thermo Fisher Scientific Inc.)], Gel-Red-based dye [for example, GelRed (manufactured by Wako Pure Chemical Industries, Ltd.), and the like], (6) compound binding to a minor groove of a DNA double helix [for example, 4',6-diamidino-2-phenylindole (DAPI) (manufactured by Thermo Fisher Scientific Inc.) and the like], and (7) compound specifically binding to an adenine-thymine (A-T) sequence [for example, pentahydrate (bis-benzimide) (Hoechst 33258) (Thermo Fisher Scientific Inc.), trihydrochloride (Hoechst 33342) (manufactured by Thermo Fisher Scientific Inc.), a bisbenzimide dye (Hoechst 34580) (manufactured by Thermo Fisher Scientific Inc.), and the like].

(a-3) Labeled Probe Method

The labeled probe method is a method in which "by using the primer pair according to the present invention and using a nucleic acid in a test sample as a template, the nucleic acid amplification reaction according to the present invention is performed, and the obtained amplification product is separated by electrophoresis. Then, the amplification product is subjected to a heat treatment so as to obtain a single-stranded amplification product. Thereafter, the amplification product is hybridized with a probe, which is labeled with a labeling substance and has a base sequence complementary to the base sequence of the amplification product, so as to obtain a hybrid, and the label in the hybrid is detected. As a result, in a case where the label in the hybrid can be detected, it is determined that 'the test sample is positive for *Chlamydia trachomatis*'".

The details of the primer pair, the labeling substance, and the labeling method using the labeling substance in the labeled probe method are as described in <1> primer set for detecting *Chlamydia trachomatis* of the present invention.

Examples of the electrophoresis in the labeled probe method include the same ones as those exemplified above for (a-1) labeled primer method, and preferable ones are also the same as those described above.

(b) Detection Method by Real-Time Method

The detection method by a real-time method is a method of detecting in real time the amplification product obtained by the nucleic acid amplification reaction according to the present invention by using the primer pair according to the present invention. Examples of specific methods thereof include (b-1) TaqMan™ probe method and (b-2) intercalator method.

(b-1) TaqMan™ Probe Method

The TaqMan™ probe method is a method in which "by using the primer pair according to the present invention and a fluorescence-labeled probe and using a nucleic acid in a test sample as a template, the nucleic acid amplification reaction (for example, real-time PCR) according to the present invention is performed. In a case where the fluorescence derived from the probe can be detected, it is determined that 'the test sample is positive for *Chlamydia trachomatis*'".

The details of the primer pair in the TaqMan™ probe method are as described in <1> *Chlamydia trachomatis* detecting primer set of the present invention.

The fluorescence-labeled probe in the TaqMan™ probe method is designed such that the probe is hybridized with a domain to be amplified in a case where the nucleic acid amplification reaction according to the present invention is performed using the primer pair according to the present invention. The 5'-terminal of the probe is labeled, for example, with a fluorescent dye (reporter fluorescent dye) and the 3'-terminal thereof is labeled, for example, with a quencher dye.

The TaqMan™ probe method will be more specifically described for (b-1-1) Case where first primer pair according to the present invention is used and (b-1-2) Case where first primer pair according to the present invention and second primer pair according to the present invention are used.

(b-1-1) Case where First Primer Pair According to the Present Invention is Used

For example, first, by using a labeled probe (first labeled probe), which is designed to be hybridized with a domain to be amplified in a case where the nucleic acid amplification reaction according to the present invention is performed using the first primer pair according to the present invention and the first primer pair according to the present invention and in which the 5'-terminal is labeled with a reporter fluorescent dye and the 3'-terminal is labeled with a quencher dye, and using a nucleic acid in a sample as a template, the nucleic acid amplification reaction according to the present invention is performed.

As a result, in a case where the fluorescence derived from the reporter fluorescent dye liberated from the first labeled probe can be detected, it is determined that "the test sample is positive for *Chlamydia trachomatis*".

(b-1-2) Case where First Primer Pair According to the Present Invention and Second Primer Pair According to the Present Invention are Used For example, first, by using the first primer pair according to the present invention, a labeled probe (first labeled probe) which is designed to be hybridized with a domain to be amplified in a case where the nucleic acid amplification reaction according to the present invention is performed using the first primer pair according to the present invention and in which the 5'-terminal is labeled with a reporter fluorescent dye and the 3'-terminal is labeled with a quencher dye, the second primer pair according to the present invention, a labeled probe (second labeled probe) which is designed to be hybridized with a domain to be amplified in a case where the nucleic acid amplification reaction according to the present invention is performed using the second primer pair according to the present invention and in which the 5'-terminal is labeled with a reporter fluorescent dye and the 3'-terminal is labeled with a quencher dye, and a nucleic acid in a sample as a template, the nucleic acid amplification reaction according to the present invention is performed.

As a result, in a case where at least either the fluorescence derived from the reporter fluorescent dye liberated from the first labeled probe or the fluorescence derived from the reporter fluorescent dye liberated from the first labeled probe is detected, it is determined that "the test sample is positive for *Chlamydia trachomatis*".

The reporter of the first labeled probe and the reporter of the second labeled probe in the method may have different fluorescence wavelengths.

It should be noted that the base sequence of the first labeled probe is different from that of the second labeled probe.

It should be noted that specific examples of the second primer pair according to the present invention include primer pairs composed of a combination of a forward primer consisting of a base sequence represented by any of SEQ ID NOS: 7 to 9 and a reverse primer consisting of a base sequence represented by SEQ ID NO: 10. Among these, a primer pair composed of a combination of a forward primer consisting of a base sequence represented by SEQ ID NO: 7 or 8 and a reverse primer consisting of a base sequence represented by SEQ NO: 10 is preferable, and a primer pair composed of a combination of a forward primer consisting of a base sequence represented by SEQ ID NO: 7 and a reverse primer consisting of a base sequence represented by SEQ ID NO: 10 is more preferable.

In the TaqMan™ probe method in (b-1-1) and (b-1-2), in addition to the primer pair according to the present invention, a primer pair for detecting *Neisseria gonorrhoeae* or microbes such as bacteria selected as an internal control may be additionally used to perform the nucleic acid amplification reaction according to the present invention. The microbes may be detected using the TaqMan™ probe method in the same manner as that described above or detected by a known method.

(b-2) Intercalator Method

The intercalator method is a method in which "by using the primer pair according to the present invention and an intercalator and using a nucleic acid in a test sample as a template, the nucleic acid amplification reaction (for example, real-time PCR) according to the present invention is performed. Then, the fluorescence derived from the intercalator performing intercalation in correlation with the amplification amount of the obtained amplification product is detected. In a case where the fluorescence derived from the intercalator can be detected as a result, a diagnosis that 'the test sample is positive for *Chlamydia trachomatis*' is made".

The details of the primer pair in the intercalator method are as described in <1> primer set for detecting *Chlamydia trachomatis* of the present invention.

Examples of the intercalator in the intercalator method are the same as those exemplified above for (a-2) intercalator method.

Hereinbelow, preferred specific examples of the method for detecting *Chlamydia trachomatis* of the present invention will be described as a method for detecting an amplification product, for a case where (a'-1) labeled primer method is used and a case where (b'-1) TaqMan™ probe method is used.

(a'-1) Labeled Primer Method

Hereinbelow, specific examples of the method for detecting *Chlamydia trachomatis* of the present invention in a case where a labeled primer method is used will be described for (a'-1-1) Case where first primer pair according to the present invention is used and (a'-1-2) Case where first primer pair according to the present invention and second primer pair according to the present invention are used.

(a'-1-1) Case where First Primer Pair According to the Present Invention is Used First, according to a known method, purified DNA is obtained from a sample from which *Chlamydia trachomatis* will be detected.

Meanwhile, for example, by using a DNA synthesizer, the first primer pair according to the present invention (that is, a forward primer consisting of a base sequence represented by SEQ ID NO: 5 and a reverse primer consisting of a base sequence represented by SEQ ID NO: 6) is synthesized by a phosphoramidite method. Then, by a known method, at least one of the primers in the first primer pair according to the present invention is labeled with a labeling substance (for example, a fluorescent substance).

By using the first primer pair according to the present invention that contains a primer labeled with a labeling substance as a primer for amplification, the nucleic acid amplification reaction (for example, PCR) according to the present invention is performed as below on the purified DNA obtained from the sample.

That is, a 10 mM buffer (for example, Tris-HCl buffer) with pH 7 to 9 is prepared which contains primers each having a concentration of 0.1 to 2 μM. and constituting the first primer pair according to the present invention, a salt (for example, $MgCl_2$) at 1.0 to 4.0 mM, a polypeptide (for example, BSA) at 80 to 150 μg/mL, a 0.8% to 1.5% surfactant (for example, polyethylene glycol), a 0.1% to 0.5% preservative (for example, ProClin 300), nucleic acid synthesis substrates (for example, dATP, dCTP, dGTP, dTTP) each having a concentration of 0.2 to 0.3 mM, and a nucleic acid synthase (for example, Taq DNA polymerase) at 10 to 80 units/ml, and the prepared buffer is used as a reaction solution for the nucleic acid amplification reaction according to the present invention. The purified DNA is added in an amount of 1 to 100 ng to 20 to 30 μL of the reaction solution for the nucleic acid amplification reaction according to the present invention, thereby obtaining a sample for the nucleic acid amplification reaction according to the present invention.

By using the sample for the nucleic acid amplification reaction according to the present invention and using a nucleic acid amplification device such as a thermal cycler, the nucleic acid amplification reaction (for example, PCR) according to the present invention is performed.

That is, after heating the sample for 1 to 10 minutes at a temperature of 93° C. to 98° C., 30 to 45 cycles are performed which each includes (1) heating the sample for 10 to 30 seconds at a temperature of 93° C. to 98° C.→(2) heating the sample for 10 to 30 seconds at a temperature of 50° C. to 70° C.→(3) heating the sample for 30 seconds to 5 minutes at a temperature of 68° C. to 72° C.

Thereafter, the obtained nucleic acid amplification product is subjected to electrophoresis (for example, capillary electrophoresis), and then the label in the amplification product is detected.

As a result, in a case where the label in the obtained nucleic acid amplification product can be detected as the number of base pairs (148 base pairs) of the product amplified by the first primer pair according to the present invention, it is determined that "the sample is positive for *Chlamydia trachomatis*".

It should be noted that in a case where capillary electrophoresis is performed using a full automatic microchip-type capillary electrophoresis device such as 2100 Bioanalyzer (manufactured by Agilent Technologies), in the obtained data; the abscissa shows electrophoresis time, and the ordinate shows fluorescence intensity. The electrophoresis time on the abscissa can be converted into the size of DNA or the like on the basis of the electrophoresis time of a molecular weight marker. Therefore, the length (number of base pairs) of the nucleic acid amplification product obtained by the nucleic acid amplification reaction according to the present invention using the first primer pair according to the present invention may be calculated in advance so as to check "whether or not the obtained nucleic acid amplification product corresponds to the calculated nucleic acid amplification product".

That is, by using the first primer pair according to the present invention in which at least one of the primers is labeled with a fluorescent substance, the nucleic acid amplification reaction (for example, PCR) according to the present invention is performed in the same manner as that described above.

Meanwhile, the length (number of base pairs) of the nucleic acid amplification product to be amplified by the nucleic acid amplification reaction (for example, PCR) according to the present invention, in which the first primer pair according to the present invention is used, is calculated in advance.

In a case where the first primer pair according to the present invention is used, in the complete base sequence of the cryptic plasmid, a nucleic acid constituted with 148 base pairs of a base sequence represented by SEQ ID NO: 2 is predicted to be amplified.

Subsequently, the obtained nucleic acid amplification product is subjected to capillary electrophoresis by using, for example, a full automatic microchip-type capillary electrophoresis device such as 2100 Bioanalyzer (manufactured by Agilent Technologies). Then, the data of the sample obtained by the capillary electrophoresis is converted into a gel image by using software attached to the device.

As a result, in a case where the length (number of base pairs) of the obtained nucleic acid amplification product is found to be the same as that of the nucleic acid amplification product constituted with 148 base pairs, it is determined that "the sample is positive for *Chlamydia trachomatis*".

(a'-1-2) Case where First Primer Pair According to the Present Invention and Second Primer Pair According to the Present Invention are Used First, according to a known method, purified DNA is obtained from a sample from which *Chlamydia trachomatis* will be detected.

Meanwhile, for example, by using a DNA synthesizer, the first primer pair according to the present invention (that is, a forward primer consisting of a base sequence represented by SEQ ID NO: 5 and a reverse primer consisting of a base sequence represented by SEQ ID NO: 6) and the second primer pair according to the present invention (for example, a forward primer consisting of a base sequence represented by SEQ ID NO: 7 and a reverse primer consisting of a base sequence represented by SEQ ID NO: 10) are synthesized by a phosphoramidite method. Then, at least one of the primers in the first primer pair according to the present invention and at least one of the primers in the second primer pair according to the present invention are labeled with a labeling substance (for example, a fluorescent substance).

By using the first primer pair according to the present invention and the second primer pair according to the present invention that contain primers labeled with a labeling substance as primers for amplification, the nucleic acid amplification reaction (for example, multiplex PCR) according to the present invention is performed as below on the purified DNA obtained from the sample.

That is, a 10 mM buffer (for example, Tris-HCl buffer) with pH 7 to 9 is prepared which contains primers each having a concentration of 0.1 to 2 μM and constituting the first primer pair according to the present invention, primers each having a concentration of 0.1 to 2 μM and constituting the second primer pair according to the present invention, a salt (for example, MgCl$_2$) at 1.0 to 4.0 mM, a polypeptide (for example, BSA) at 80 to 150 µg/mL, a 0.8% to 1.5% surfactant (for example, polyethylene glycol), a 0.1% to 0.5% preservative (for example, ProClin 300), nucleic acid synthesis substrates (for example, dATP, dCTP, dGTP; and dTTP) each having a concentration of 0.2 to 0.3 mM, and a nucleic acid synthase (for example, Taq DNA polymerase) at 10 to 80 units/ml, and the prepared buffer is used as a reaction solution for the nucleic acid amplification reaction according to the present invention. The purified DNA sample of *Chlamydia trachomatis* is added in an amount of 1 to 100 ng to 20 to 30 µL of the reaction solution for the nucleic acid amplification reaction according to the present invention, thereby obtaining a sample for the nucleic acid amplification reaction according to the present invention.

By using the sample for the nucleic acid amplification reaction according to the present invention and using a nucleic acid amplification device such as a thermal cycler, the nucleic acid amplification reaction (for example, multiplex PCR) according to the present invention is performed.

That is, after heating the sample for 1 to 10 minutes at a temperature of 93° C. to 98° C., 30 to 45 cycles are performed which each includes (1) heating the sample for 10 to 30 seconds at a temperature of 93° C. to 98° C.→(2) heating the sample for 10 to 30 seconds at a temperature of 50° C. to 70° C.→(3) heating the sample for 30 seconds to 5 minutes at a temperature of 68° C. to 72° C.

Thereafter, each of the obtained nucleic acid amplification products is subjected to electrophoresis (for example, capillary electrophoresis), and then the label in the amplification product is detected.

As a result, in a case where at least either a case where the label in the obtained nucleic acid amplification product can be detected as the number of base pairs (148 bases) of the product amplified by the first primer pair according to the present invention or a case where the label in the obtained nucleic acid amplification product can be detected as the number of base pairs (173 bases) of the product amplified by the second primer pair according to the present invention is shown, it is determined that "the sample is positive for *Chlamydia trachomatis*".

It should be noted that in a case where the capillary electrophoresis is performed using a full automatic microchip-type capillary electrophoresis device such as 2100 Bioanalyzer (manufactured by Agilent Technologies), in the obtained data, the abscissa shows electrophoresis time and the ordinate shows fluorescence intensity. The electrophoresis time on the abscissa can be converted into the size of DNA or the like on the basis of the electrophoresis time of a molecular weight marker. Therefore, the length (number of base pairs) of the nucleic acid amplification product obtained by the nucleic acid amplification reaction according to the present invention by using the first primer pair according to the present invention and the length (number of base pairs) of the nucleic acid amplification product obtained by the nucleic acid amplification reaction according to the present invention by using the second primer pair according to the present invention may be calculated in advance so as to check "whether or not the obtained nucleic acid amplification product corresponds to the calculated nucleic acid amplification product".

That is, by using the first primer pair according to the present invention and the second primer pair according to the present invention in which at least one of the primers constituting each of the first and second primer pairs is labeled with a fluorescent substance, the nucleic acid amplification reaction (for example, multiplex PCR) according to the present invention is performed.

Meanwhile, the length (number of base pairs) of the nucleic acid amplification product to be amplified by the nucleic acid amplification reaction (for example, PCR) according to the present invention, in which the first primer pair according to the present invention is used, and the length (number of base pairs) of the nucleic acid amplification product to be amplified by the nucleic acid amplification reaction (for example, PCR) according to the present invention, in which the second primer pair according to the present invention (for example, a forward primer which has a base sequence represented by SEQ ID NO: 7 and a reverse primer which has a base sequence represented by SEQ ID NO: 10) is used, are calculated in advance.

In a case where the first primer pair according to the present invention is used, in the complete base sequence of the cryptic plasmid, a nucleic acid constituted with 148 base pairs of a base sequence represented by SEQ ID NO: 2 is predicted to be amplified.

In contrast, in a case where the second primer pair according to the present invention is used, in the complete base sequence of the CT genomic DNA, a nucleic acid constituted with 173 base pairs of a base sequence represented by SEQ ID NO: 3 is predicted to be amplified.

Subsequently, the obtained nucleic acid amplification product is subjected to capillary electrophoresis by using, for example, a full automatic microchip-type capillary electrophoresis device such as 2100 Bioanalyzer (manufactured by Agilent Technologies). Then, the data of the sample obtained by the capillary electrophoresis is converted into a gel image by using software attached to the device.

As a result, in a case where the obtained nucleic acid amplification product is the same as at least any of the nucleic acid amplification product constituted with 148 base pairs and the nucleic acid amplification product constituted with 173 base pairs, it is determined that "the sample is positive for *Chlamydia trachomatis*".

(b'-1) TaqMan™ Probe Method

Hereinbelow, specific examples of the method for detecting *Chlamydia trachomatis* of the present invention in a case where the TaqMan™ probe method is used will be described for (b'-1-1) Case where first primer pair according to the present invention is used and (b'-1-2) Case where first primer pair according to the present invention and second primer pair according to the present invention are used.

(b'-1-1) Case where First Primer Pair According to the Present Invention is Used First, according to a known method, a purified DNA sample is obtained from a sample from which *Chlamydia trachomatis* will be detected.

Meanwhile, for example, by using a DNA synthesizer, the first primer pair according to the present invention (that is, a forward primer consisting of a base sequence represented by SEQ ID NO: 5 and a reverse primer consisting of a base sequence represented by SEQ ID NO: 6) is synthesized by a phosphoramidite method.

In addition, from a base sequence to be amplified by the nucleic acid amplification reaction (for example, PCR) according to the present invention in which the first primer pair according to the present invention is used, a sequence to be used as a probe is designed, and an oligonucleotide having the base sequence is synthesized. By a known method, the 5'-terminal of the oligonucleotide is bonded to FAM which is a reporter fluorescent dye, and the 3'-terminal of the oligonucleotide is bonded to TAMRA which is a quencher dye. In this way, a fluorescence-labeled probe (first labeled probe) is obtained.

By using the first primer pair according to the present invention synthesized as above as a primer for amplification, the nucleic acid amplification reaction (for example, real-time PCR) according to the present invention is performed as shown below, for example.

That is, a 10 mM buffer (for example, Tris-HCl buffer) with pH 8 to 9 is prepared which contains primers each having a concentration of 0.1 to 2 µM and constituting the first primer pair according to the present invention, the first labeled probe at 0.1 to 1 µM, a salt (for example, $MgCl_2$) at 1.0 to 4.0 mM, a salt (for example, KCl) at 50 to 100 mM, a polypeptide (for example, BSA) at 300 to 600 µg/mL, a 0.05% to 2% surfactant (for example, sodium cholate), nucleic acid synthesis substrates (for example, dATP, dCTP, dGTP, and dTTP) each having a concentration of 0.1 to 0.3 mM, and a nucleic acid synthase (for example, Taq DNA polymerase) at 10 to 80 units/mL, and the prepared buffer is used as a reaction solution for the nucleic acid amplification reaction according to the present invention. The purified DNA sample of *Chlamydia trachomatis* is added in an amount of 1 to 100 ng to 20 to 25 µL of the reaction solution for the nucleic acid amplification reaction according to the present invention, thereby obtaining a sample for the nucleic acid amplification reaction according to the present invention.

By using the sample for the nucleic acid amplification reaction according to the present invention and using a thermal cycler or the like, the nucleic acid amplification reaction (for example, real-time PCR) according to the present invention is performed.

That is, after heating the sample for 5 to 15 minutes at a temperature of 93° C. to 98° C., 30 to 55 cycles are performed which each includes (1) heating the sample for 10 to 30 seconds at a temperature of 93° C. to 98° C.→(2) heating the sample for 30 to 90 seconds at a temperature of 50° C. to 70° C. Furthermore, the fluorescence intensity derived from the reporter fluorescent dye is measured in each cycle.

In a case where the fluorescence derived from the reporter fluorescent dye is measured, it is determined that "positive for *Chlamydia trachomatis*".

Furthermore, by creating a calibration curve by a known method, the number of *Chlamydia trachomatis* in the sample can be calculated.

(b'-1-2) Case where First Primer Pair According to the Present Invention and Second Primer Pair According to the Present Invention are Used First, according to a known method, a purified DNA sample is obtained from a sample from which *Chlamydia trachomatis* will be detected.

In addition, for example, by using a DNA synthesizer, the first primer pair according to the present invention (that is, a forward primer consisting of a base sequence represented by SEQ ID NO: 5 and a reverse primer consisting of a base sequence represented by SEQ ID NO: 6) and the second primer pair according to the present invention (for example, a forward primer consisting of a base sequence represented by SEQ ID NO: 7 and a reverse primer consisting of a base sequence represented by SEQ ID NO: 10) are synthesized by a phosphoramidite method.

Then, from a base sequence to be amplified by the nucleic acid amplification reaction (for example, PCR) according to the present invention in which the first primer pair according to the present invention is used, a sequence to be used as a probe is designed, and an oligonucleotide having the base sequence is synthesized. By a known method, the 5'-terminal of the oligonucleotide is bonded to FAM which is a reporter fluorescent dye, and the 3'-terminal of the oligonucleotide is bonded to TAMRA which is a quencher dye. In this way, a fluorescence-labeled probe (first labeled probe) is obtained.

In addition, from a base sequence to be amplified by the nucleic acid amplification reaction (for example, PCR) according to the present invention in which the second primer pair according to the present invention (for example, a forward primer consisting of a base sequence represented by SEQ ID NO: 7 and a reverse primer consisting of a base sequence represented by SEQ ID NO: 10) is used, a sequence to be used as a probe is designed, and an oligonucleotide having the base sequence is synthesized. By a known method, the 5'-terminal of the oligonucleotide is bonded to HEX which is a reporter fluorescent dye, and the 3'-terminal of the oligonucleotide is bonded to TAMRA which is a quencher dye. In this way, a fluorescence-labeled probe (second labeled probe) is obtained.

By using the first primer pair according to the present invention and the second primer pair according to the present invention that are synthesized as above as primers for amplification, the nucleic acid amplification reaction (for example, real-time PCR) according to the present invention is performed as below, for example.

That is, a 10 mM buffer (for example, Tris-HCl buffer) with pH 8 to 9 is prepared which contains primers each having a concentration of 0.1 to 2 µM and constituting the first primer pair according to the present invention, primers each having a concentration of 0.1 to 2 µM and constituting the second primer pair according to the present invention, the first labeled probe at 0.1 to 1 µM, the second labeled probe at 0.1 to 1 µM, a salt (for example, $MgCl_2$) at 1.0 to 4.0 mM, a salt (for example, KCl) at 50 to 100 mM, a polypeptide (for example, BSA) at 300 to 600 µg/mL, a 0.05% to 2% surfactant (for example, sodium cholate), nucleic acid synthesis substrates (for example, dATP, dCTP, dGTP, and dTTP) each having a concentration of 0.1 to 0.3 mM, and a nucleic acid synthase (for example, Taq DNA polymerase) at 10 to 80 units/mL, and the prepared buffer is used as a reaction solution for the nucleic acid amplification reaction according to the present invention. The purified DNA sample of *Chlamydia trachomatis* is added in an amount of 1 to 100 ng to 20 to 25 µL of the reaction solution for the nucleic acid amplification reaction according to the present invention, thereby obtaining a sample for the nucleic acid amplification reaction according to the present invention.

By using the sample for the nucleic acid amplification reaction according to the present invention and using a thermal cycler or the like, the nucleic acid amplification reaction (for example, real-time PCR) according to the present invention is performed.

That is, after heating the sample for 5 to 15 minutes at a temperature of 93° C. to 98° C. 30 to 55 cycles are performed which each includes (1) heating the sample for 10 to 30 seconds at a temperature of 93° C. to 98° C.→(2) heating the sample for 30 to 90 seconds at a temperature of 50° C. to 70° C. Furthermore, the fluorescence intensity derived from the reporter fluorescent dye is measured in each cycle.

As a result, in a case where at least either the fluorescence derived from the first labeled probe or the fluorescence derived from the second labeled probe is detected, it is determined that "the sample is positive for *Chlamydia trachomatis*".

Furthermore, by creating a calibration curve by a known method, the number of *Chlamydia trachomatis* in the sample can be calculated.

<3> Reagent Kit for Detecting *Chlamydia Trachomatis* of the Present Invention

The reagent kit for detecting *Chlamydia trachomatis* of the present invention (hereinafter, simply described as a reagent kit of the present invention in some cases) contains a first primer pair composed of a combination of a forward primer consisting of a base sequence represented by SEQ ID NO: 5 and a reverse primer consisting of a base sequence represented by SEQ ID NO: 6.

Furthermore, in the reagent kit of the present invention, the second primer pair according to the present invention may be additionally used. Specifically, for example, the reagent kit may contain a primer set containing a first primer pair composed of a combination of a forward primer consisting of a base sequence represented by SEQ ID NO: 5 and a reverse primer consisting of a base sequence represented by SEQ ID NO: 6 and a second primer pair composed of a combination of a forward primer consisting of a base sequence represented by any of SEQ ID NOS: 7 to 9 and a reverse primer consisting of a base sequence represented by SEQ ID NO: 10.

In a case where the reagent kit of the present invention contains the first primer pair and the second primer pair according to the present invention, (1) or (2) in Table 2 shown below is preferable, and (1) is more preferable.

TABLE 2

| | First primer pair | | Second primer pair | |
|---|---|---|---|---|
| (1) | Forward primer | SEQ ID NO: 5 | Forward primer | SEQ ID NO: 7 |
| | Reverse primer | SEQ ID NO: 6 | Reverse primer | SEQ ID NO: 10 |
| (2) | Forward primer | SEQ ID NO: 5 | Forward primer | SEQ ID NO: 8 |
| | Reverse primer | SEQ ID NO: 6 | Reverse primer | SEQ ID NO: 10 |

In the reagent kit of the present invention, at least one of the primers according to the present invention may be labeled with a labeling substance.

For example, in a case where the reagent kit of the present invention contains the primer according to the present invention that is labeled with a labeling substance and contains only the first primer pair according to the present invention as primers for detecting CT, at least one of the forward primer and the reverse primer may be labeled with a labeling substance.

For example, in a case where the reagent kit of the present invention contains the primers according to the present invention that are labeled with a labeling substance and contains two primer pairs including the first primer pair according to the present invention and the second primer pair according to the present invention, at least either the forward primer or the reverse primer of the first primer pair according to the present invention and at least either the forward primer or the reverse primer of the second primer pair according to the present invention may be labeled with a labeling substance.

The details of the primers, the primer pairs, the primer set, and the labeling substance contained in the reagent kit of the present invention and the method for labeling the primers with the labeling substance are as described in <1> primer set for detecting *Chlamydia trachomatis* of the present invention.

The reagent kit of the present invention may contain, in addition to the primer pair according to the present invention for detecting *Chlamydia trachomatis*, a primer pair for detecting *Neisseria gonorrhoeae* or a primer pair for detecting bacteria selected as an internal control, a nucleic acid derived from the bacteria, and the corresponding bacteria.

It should be noted that in the reagent kit of the present invention, each of the primers constituting the primer pair for detecting *Neisseria gonorrhoeae* and the primer pair for detecting the internal control may be labeled with a labeling substance.

For example, in a case where the reagent kit of the present invention contains the primer pair for detecting *Neisseria gonorrhoeae* that is labeled with a labeling substance, at least either the forward primer or the reverse primer of the primer pair for detecting *Neisseria gonorrhoeae* may be labeled with a labeling substance.

For example, in a case where the reagent kit of the present invention contains the primer pair for detecting the internal control that is labeled with a labeling substance, at least either the forward primer or the reverse primer of the primer pair for detecting the internal control may be labeled with a labeling substance.

For example, in a case where the reagent kit of the present invention contains the primer pair for detecting *Neisseria gonorrhoeae* and the primer pair for detecting the internal control that are labeled with a labeling substance, at least either the forward primer or the reverse primer of the primer pair for detecting *Neisseria gonorrhoeae* and at least either the forward primer or the reverse primer of the primer pair for detecting the internal control may be labeled with a labeling substance.

The reagent kit of the present invention can contain reagents generally used in the field of the related art, such as a buffer, a stabilizing agent, and preservative which do not reduce the stability of a coexisting reagent or the like and do not inhibit a nucleic acid amplification reaction such as PCR or a hybridization reaction. In addition, the concentration thereof may be appropriately selected within a range of concentration that is generally used in the field of the related art.

Specific examples of the buffer include all the buffers used in a case where a general nucleic acid amplification reaction such as PCR or a hybridization reaction is performed, such as a tris-buffer, a phosphate buffer, a veronal buffer, a borate buffer, and a Good's buffer. The pH thereof is not particularly limited, but is preferably within a range of 5 to 9 in general.

If necessary, the reagent kit of the present invention can contain a nucleic acid synthase (for example, Taq DNA polymerase and the like), a nucleic acid synthesis substrate (for example, dATP, dCTP, dGTP, dTTP, and the like), an intercalator (for example, ethidium bromide, SYBR™ Green I, and the like), a labeling substance (for example, FAM, TAMRA, and the like), a fluorescence-labeled probe, a reagent for electrophoresis (for example, gel), a DNA marker, and the like.

Furthermore, the reagent kit of the present invention may contain an instruction for describing the method for detecting *Chlamydia trachomatis* of the present invention or for determining a presence or absence of *Chlamydia trachomatis*, and the like. The "instruction" means an instruction manual of the kit that more effectively describes the characteristics, principles, operation sequence, determination sequence, and the like in the method by sentences or diagrams, sentences attached thereto, a brochure, and the like.

Hereinafter, the present invention will be specifically described based on examples, but the present invention is not limited to the examples.

EXAMPLES

All the bacteria used in the examples are clinical isolates, and the bacterial species thereof are identified in advance through the formation of a colony, various biochemical tests, and the like of the related art after culture.

Example 1 Detection of *Chlamydia Trachomatis* by Using First Primer Pair According to the Present Invention (1) Primer Pair (First Primer Pair According to the Present Invention)

A forward primer (CT1P1F-2) and a reverse primer (CT1P1R-9) consisting of base sequences shown in the following Table 3 were used. It should be noted that as the forward primer (CT1P1F-2), a primer in which the 5'-terminal of the sequence thereof is labeled with a fluorescent substance TAMRA was used.

TABLE 3

| Primer | Base sequence | SEQ ID NO: |
|---|---|---|
| Forward CT1P1F-2 | 5'-ccgctcaaggaccagcaaataatc-3' | 5 |
| Reverse CI1P1R-9 | 5'-aagctttttccgcatccaaacca-3' | 6 |

(2) Target Sequence

In the complete base sequence (GenBankID: HE603230.1) of the cryptic plasmid, a base sequence including a domain (SEQ ID NO: 2: 148 base pairs) constituted with the $4,770^{th}$ to $4,917^{th}$ bases is a target sequence of the first primer pair (CT1P1F-2 and CT1P1R-9) according to the present invention.

(3) Preparation of *Chlamydia* DNA

Each of the *Chlamydia* bacteria (genus *Chlamydia*: *Chlamydia Trachomatis*, genus *Chlamydophila*: *Chlamydophila caviae*, *Chlamydophila pneumoniae*, *Chlamydophila psittaci*, *Chlamydophila pecorum*) shown in the following Table 4 was cultured according to a known method. Then, by using a known nucleic acid purification method, purified genomic DNA was obtained. The number of copies of each of the obtained purified DNA was calculated using SYBR™ Premix Ex Taq™ II (manufactured by Takara Bio Inc.) and a real-time PCR device [StepOnePlus™ (manufactured by Thermo Fisher Scientific Inc.)]. The purified DNA was prepared as a solution having a concentration of $10^5$ copy/µL by using a TE buffer (pH 8.0) (manufactured by NIPPON GENE CO., LTD.), and used as *Chlamydia* DNA.

It should be noted that all the bacterial strains used were offered from the laboratory of Professor Kumon Hiromi in Graduate School of Medicine Dentistry and Pharmaceutical Sciences, Okayama University.

TABLE 4

| Species | Strain |
|---|---|
| *C. caviae* | GPIC |
| *C. pneumoniae* | KKpn |
| | TW183 |

TABLE 4-continued

| Species | Strain |
|---|---|
| *C. pssitaci* | cal10 |
| | 6BC |
| | Budgerigan-1 |
| *C. trachomatis* | A (Serovar) |
| | B (Serovar) |
| | Ba (Serovar) |
| | C (Serovar) |
| | D (Serovar) |
| | E (Serovar) |
| | F (Serovar) |
| | G (Serovar) |
| | H (Serovar) |
| | I (Serovar) |
| | J (Serovar) |
| | K (Serovar) |
| | L1 (Serovar) |
| | L2 (Serovar) |
| | L3 (Serovar) |

(4) PCR

A 10 mM Tris-HCl buffer (pH 8.0) was prepared which contained primers descried in the section (1) (CT1P1F-2 and CT1P1R-9) each having a concentration of 0.8 µM, 1.2 mM $MgCl_2$, BSA at 100 µg/mL, 1% polyethylene glycol, 0.2% ProClin 300 (manufactured by Sigma-Aldrich Co. LLC.), dATP, dCTP, dGTP, and dTTP (manufactured by Toyobo Co., Ltd) each having a concentration of 0.25 mM, and KOD Exo(−) (manufactured by Toyobo Co., Ltd) at 60 units/mL, and the prepared buffer was used as a reaction solution for PCR.

Each *Chlamydia* DNA prepared in the section (3) was suspended in an amount of 1 µL in 25 µL of the obtained reaction solution for PCR, and the obtained resultant was used as a sample for PCR.

A 96-well plate (manufactured by Thermo Fisher Scientific Inc.) was filled with the sample for PCR, and by using StepOnePlus™ (manufactured by Thermo Fisher Scientific Inc.), PCR was performed. After heating the sample for 2 minutes at 95° C., 40 cycles were performed which each includes (1) heating the sample for 10 seconds at 97° C.→(2) heating the sample for 20 seconds at 65.5° C.→(3) heating the sample for 30 seconds at 71.5° C.

Then, by using a full automatic microchip-type capillary electrophoresis device 2100 Bioanalyzer (manufactured by Agilent Technologies), the obtained nucleic acid amplification product was subjected to capillary electrophoresis according to the protocol attached to the device. In this way, the obtained nucleic acid amplification product was separated and detected.

(5) Result

The results of the capillary electrophoresis are summarized in the following Table 5. In Table 5, "Positive" in the column of "Result" shows that a target nucleic acid amplification product of 148 base pairs was detected, and "Negative" in the same column shows that a target nucleic acid amplification product was not detected.

TABLE 5

| Species | Strain | Results |
|---|---|---|
| *C. caviae* | GPIC | Negative |
| *C. pneumoniae* | KKpn | Negative |
| | TW183 | Negative |
| *C. pssitaci* | cal10 | Negative |
| | 6BC | Negative |
| | Budgerigan-1 | Negative |

TABLE 5-continued

| Species | Strain | Results |
| --- | --- | --- |
| C. trachomatis | A (Serovar) | Positive |
|  | B (Serovar) | Positive |
|  | Ba (Serovar) | Positive |
|  | C (Serovar) | Positive |
|  | D (Serovar) | Positive |
|  | E (Serovar) | Positive |
|  | F (Serovar) | Positive |
|  | G (Serovar) | Positive |
|  | H (Serovar) | Positive |
|  | I (Serovar) | Positive |
|  | J (Serovar) | Positive |
|  | K (Serovar) | Positive |
|  | L1 (Serovar) | Positive |
|  | L2 (Serovar) | Positive |
|  | L3 (Serovar) | Positive |

As is evident from the results shown in Table 5, only in a case where PCR was performed using the first primer pair according to the present invention and using the DNA sample derived from each of the *Chlamydia trachomatis* strains as a template, a target nucleic acid amplification product was confirmed, and it is determined that those samples are positive for *Chlamydia trachomatis* could be made.

In contrast, in a case where PCR was performed using DNA samples derived from bacteria other than *Chlamydia trachomatis* as a template, the corresponding target nucleic acid amplification product was not confirmed, and it is determined that these samples are negative for *Chlamydia trachomatis* could be made.

From the above results, it was understood that by performing a nucleic acid amplification reaction by using the first primer pair according to the present invention, *Chlamydia trachomatis* can be specifically detected.

Example 2 and Comparative Examples 1 and 2
Influence of Human Genomic DNA on PCR Performed Using Various Primer Pairs (1) Primer Pair First primer pair according to the present invention (Example 2)

The same primer pair as that in Example 1 was used.

Primer pair of Patent Literature 1 (Comparative Example 1)

As the primer pair disclosed in Patent Literature 1 (JP5811086B), a forward primer (IshikFw) and a reverse primer (IshikRv) each consisting of base sequences shown in the following Table 6 were used.

It should be noted that as the reverse primer (IshikRv), a primer in which the 5'-terminal of the sequence thereof was labeled with a fluorescent substance TAMRA was used.

Primer pair of Non-Patent Literature 1 (Comparative Example 2)

As the primer pair disclosed in Non-Patent Literature 1 (Moller, J. K., et al., Journal of Clinical Microbiology, 2008, 46, p. 3892-3895), a forward primer (MollarFw) and a reverse primer (MollarRv) consisting of base sequences shown in the following Table 6 were used.

It should be noted that as the forward primer (MollarFw), a primer in which the 5'-terminal of the sequence thereof was labeled with a fluorescent substance TAMRA was used.

The primer pairs used are summarized in the following Table 6,

TABLE 6

|  | Primer |  | Base sequence | SEQ ID NO: |
| --- | --- | --- | --- | --- |
| Example 2 | Forward | CT1P1F-2 | 5'-ccgctcaaggac cagcaaataatc-3' | 5 |
|  | Reverse | CT1P1R-9 | 5'-aagctttttccg catccaaacca-3' | 6 |
| Comparative Example 1 | Forward | IshikFw | 5'-cgctcaaggacc agcaaata-3' | 11 |
|  | Reverse | IshikRv | 5'-gcttttccgca tccaaac-3' | 12 |
| Comparative Example 2 | Forward | MollarFw | 5'-ccgctcaaggac cagcaa-3' | 13 |
|  | Reverse | MollarRv | 5'-agaagcattggt tgatgaatt-3' | 14 |

(2) Preparation of Human Genomic DNA

From the human whole blood of a normal individual (*Chlamydia trachomatis* non-infected individual), DNA was purified using a NucleoSpin™ Blood XL kit (MACHEREY-NAGEL GmbH & Co. KG). Then, the DNA was concentrated using Etachinmate (manufactured by NIPPON GENIE CO., LTD.) and prepared as a solution having a concentration of 1 mg/mL by using a TE buffer (pH 8.0), and the obtained resultant was used as human genomic DNA.

(3) PCR

The following reaction solutions for PCR were prepared by the same method as that in (4) of Example 1, except that the first primer pair according to the present invention, the primer pair of Patent Literature 1, and the primer pair of Non-Patent Literature 1 were used as primer pairs.

Reaction solution for PCR containing first primer pair according to the present invention Reaction solution for PCR containing primer pair of Patent Literature 1

Reaction solution for PCR containing primer pair of Non-Patent Literature 1

The human genomic DNA prepared in the section (2) was suspended and added in an amount of 1 µL; to 25 µL of each of three kinds of reaction solutions for PCR, and the obtained resultant was used as a sample for PCR.

PCR was performed by the same method as that in (4) of Example 1 by using the sample for PCR, and then capillary electrophoresis was performed, thereby separating and detecting the nucleic acid amplification product.

(4) Result

The results of the capillary electrophoresis are shown in FIG. 1. The primer pair used in each lane in FIG. 1 is shown in the following Table 7.

In FIG. 1, a band shows that the nucleic acid amplification product was detected. It should be noted that because the sample for PCR does not contain *Chlamydia trachomatis* DNA, in a case where a band showing a nucleic acid amplification product is detected, the band shows that a nucleic acid is nonspecifically amplified (a nonspecific nucleic acid amplification product is obtained).

TABLE 7

| | Lane | Primer | | SEQ ID NO: |
|---|---|---|---|---|
| Comparative Example 2 | 1 | Forward Reverse | MollarFw MollarRv | 13 14 |
| Comparative Example 1 | 2 | Forward Reverse | IshikFw IshikRv | 11 12 |
| Example 2 | 3 | Forward Reverse | CT1P1F-2 CT1P1R-9 | 5 6 |

As is evident from the results shown in FIG. 1, in a case where PCR was performed using the first primer pair according to the present invention (lane 3: Example 2), even in the presence of the human genomic DNA, a band showing the amplification of a nucleic acid amplification product was not detected. That is, it was understood that the nucleic acid was not nonspecifically amplified.

In contrast, in a case where PCR was performed using the primer pair disclosed in Patent Literature 1 (lane 2: Comparative Example 1) and in a case where PCR was performed using the primer pair disclosed in Non-Patent Literature 1 (lane 1: Comparative Example 2), in the presence of the human genomic DNA, a large number of bands showing a nucleic acid amplification product were detected. That is, it was understood that the nucleic acid was nonspecifically amplified.

Particularly, it was understood that because the band at around 150 base pairs (lane 2: Comparative Example 1) is extremely close to 145 base pairs which constitute a target sequence of the cryptic plasmid of the primer pair disclosed in Patent Literature 1, a false positive is highly likely to occur.

From the above results, it was understood that in a case where the first primer pair according to the present invention is used, nonspecific amplification of a nucleic acid can be suppressed, and hence a false positive is hardly likely to occur.

In contrast, it was understood that in a case where the primer pair disclosed in Patent Literature 1 and the primer pair disclosed in Non-Patent Literature 1 are used, nonspecific amplification of a nucleic acid cannot be suppressed, and hence a false positive is highly likely to occur.

Example 3 and Comparative Example Detection of *Chlamydia Trachomatis* in Presence of Human Genomic DNA (1) Primer Pair
First primer pair according to the present invention (Example 3)
The same primer pair as that in Example 1 was used,
Primer pair of Non-Patent Literature 1 (Comparative Example 3)
The same primer pair as that in Comparative Example 2 was used.
The primer pairs used are summarized in the following Table 8.

TABLE 8

| | Primer | | Base sequence | SEQ ID NO: |
|---|---|---|---|---|
| Example 3 | Forward | CT1P1F-2 | 5'-ccgctcaaggac cagcaaataatc-3' | 5 |
| | Reverse | CT1P1R-9 | 5'-aagctttttccg catccaaacca-3' | 6 |

TABLE 8 -continued

| | Primer | | Base sequence | SEQ ID NO: |
|---|---|---|---|---|
| Comparative Example 3 | Forward | MollarFw | 5'-ccgctcaaggac cagcaa-3' | 13 |
| | Reverse | MollarRv | 5'-agaagcattggt tgatgaatta-3' | 14 |

(2) Target Sequence
In the complete base sequence (GenBankID: HE603230.1) of the cryptic plasmid, a base sequence including a domain (148 base pairs: SEQ ID NO: 2) constituted with the $4,770^{th}$ to $4,917^{th}$ bases is a target sequence of the first primer pair (Example 3) according to the present invention.

In the complete base sequence (GenBankID: HE603230.1) of the cryptic plasmid, a base sequence including a domain (117 base pairs: SEQ ID NO: 20) constituted with the $4,770^{th}$ to $4,886^{th}$ bases is a target sequence of the primer pair (Comparative Example 3) of Non-Patent Literature 1.

(3) Preparation of *Chlamydia* DNA
The *Chlamydia* DNA was used which was prepared in (3) of Example 1 and purified from each of *C. trachomatis* strains (A, B, Ba, C, D, E, F, G, H, I, J, K, L1, L2, and L3).

(4) Preparation of Human Genomic DNA
The human genomic DNA prepared in (2) of Example 2 was used.

(5) PCR
The following reaction solutions for PCR were prepared by the same method as that in (4) of Example 1, except that the first primer pair according to the present invention and the primer pair of Non-Patent Literature 1 were used as primer pairs.

Reaction solution for PCR containing first primer pair according to the present invention
Reaction solution for PCR containing primer pair of Non-Patent Literature 1

Each of the *Chlamydia* DNA and the human genomic DNA prepared in (3) and (4) was suspended and added in an amount of 1 μL to 25 μL of each of two kinds of the reaction solutions for PCR, thereby preparing samples for PCR.

By using these various samples for PCR, PCR and capillary electrophoresis were performed by the same method as that in (4) of Example 1, thereby separating and detecting a nucleic acid amplification product.

Figure 2:
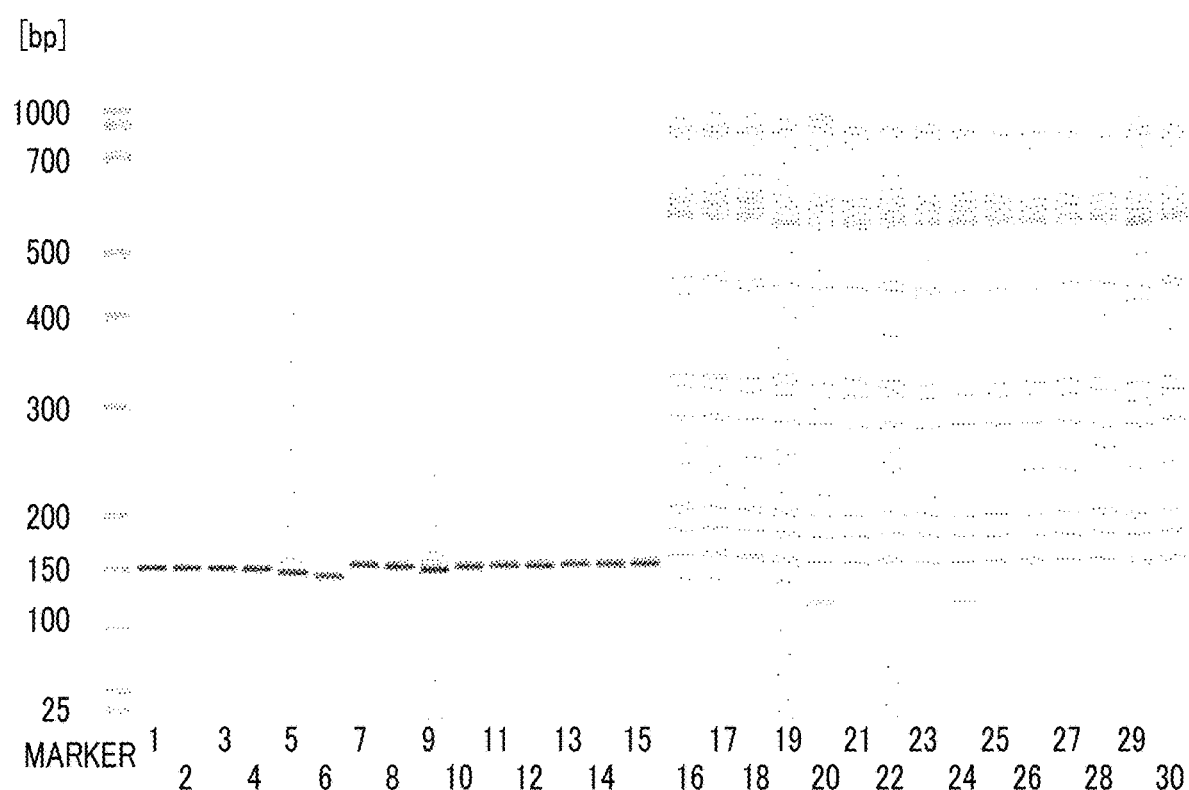
FIG. 2 is a phoretic diagram obtained by separating and detecting PCR amplification products, which are obtained in Example 3 and Comparative Example 3 from samples containing *Chlamydia trachomatis* DNA and human genomic DNA by using various primer pairs, by capillary electrophoresis.

(6) Result
FIG. 2 shows the results of the capillary electrophoresis. The relationship between each lane in FIG. 2 and the primer pair as well as the *Chlamydia* DNA used for amplification is shown in the following Table 9.

In addition, a band in FIG. 2 shows that a nucleic acid amplification product was detected.

It should be noted that in a case where the first primer pair according to the present invention was used (Example 3), and a band was detected at around 148 base pairs, because the target sequence is constituted with 148 base pairs, it can be said that *Chlamydia trachomatis* as a target could be detected.

In addition, in a case where the primer pair of Non-Patent Literature 1 was used (Comparative Example 3), and a band was detected at around 117 base pairs, because the target sequence is constituted with 117 base pairs, it can be said that *Chlamydia trachomatis* as a target could be detected.

TABLE 9

| Lane | Chlamydia DNA (serotype) | Primer | SEQ ID NO: |
|---|---|---|---|
| Example 3 | 1 A | Forward: CT1P1F-2 | 5 |
| | 2 B | Reverse: CT1P1R-9 | 6 |
| | 3 B a | | |
| | 4 C | | |
| | 5 D | | |
| | 6 E | | |
| | 7 F | | |
| | 8 G | | |
| | 9 H | | |
| | 10 I | | |
| | 11 J | | |
| | 12 K | | |
| | 13 L 1 | | |
| | 14 L 2 | | |
| | 15 L 3 | | |
| Comparative Example 3 | 16 A | Forward: MollarFw | 13 |
| | 17 B | Reverse: MollarRv | 14 |
| | 18 B a | | |
| | 19 C | | |
| | 20 D | | |
| | 21 E | | |
| | 22 F | | |
| | 23 G | | |
| | 24 H | | |
| | 25 I | | |
| | 26 J | | |
| | 27 K | | |
| | 28 L 1 | | |
| | 29 L 2 | | |
| | 30 L 3 | | |

As is evident from the results shown in FIG. 2, in a case where PCR was performed using the first primer pair according to the present invention (lanes 1 to 15: Example 3), bands were detected at around 148 base pairs for *Chlamydia trachomatis* of all serotypes, and a plurality of serotypes of *Chlamydia trachomatis* could be detected. Furthermore, a band showing the nonspecific amplification of a nucleic acid, that is, a band other than the band at around 148 base pairs was not detected.

In contrast, in a case where PCR was performed using the primer pair of Non-Patent Literature 1 (lanes 16 to 30: Comparative Example 3), for serotype D (lane 20) and serotype H (lane 24), a thin band was confirmed at around 117 base pairs. However, for other serotypes, a band was not confirmed, and not all the serotypes could be detected. In addition, a large number of bands showing the nonspecific amplification of a nucleic acid were confirmed between 150 base pairs and 1,000 base pairs.

From the above results, it was understood that in a case where the first primer pair according to the present invention is used, all the serotypes can be detected, and a false negative is hardly likely to occur. In addition, it was understood that it is possible to suppress the nonspecific nucleic acid amplification that results in a false positive.

In contrast, it was understood that in a case where the primer pair of Non-Patent Literature 1 is used, not all the serotypes of *Chlamydia trachomatis* can be detected. Furthermore, it was understood that it is impossible to suppress the nonspecific nucleic acid amplification that results in a false positive.

Example 4 Detection of *Chlamydia Trachomatis* b Using First Primer Pair According to the Present Invention and Second Primer Pair According to the Present Invention (1) Primer Pair
First primer pair according to the present invention
The same primer pair as that in Example 1 was used.
Second primer pair according to the present invention
A forward primer (CT2F-4) and a reverse primer (CT2_8) consisting of the base sequences shown in the following Table 10 were used.
It should be noted that as the reverse primer (CT2_8), a primer in which the 5'-terminal of the sequence thereof was labeled with a fluorescent substance TAMRA was used.
The reverse primer (CT2_8) is disclosed in SeqID92 in WO93/00447.
Primer pair for detecting *Neisseria gonorrhoeae*
A forward primer (NG21F) and a reverse primer (NG24R) consisting of the base sequences shown in the following Table 10 were used.
It should be noted that as the reverse primer (NG24R), a primer in which the 5'-terminal of the sequence thereof was labeled with a fluorescent substance TAMRA was used.
The forward primer (NG21F) is a primer obtained by deleting 5 bases of the 5'-terminal of the sequence disclosed in SeqID12 in WO96/12824 and adding 2 bases to the 3'-terminal thereof. The reverse primer (NG24R) is disclosed in SeqID108 in WO93/00447.
The primer pair for detecting *Neisseria gonorrhoeae* was used for verifying whether or not *Chlamydia trachomatis* can be detected using the primer set, which contains the first primer pair according to the present invention and the second primer pair according to the present invention, even in the presence of the primer pair.
The primer pairs used are summarized in the following Table 10.

TABLE 10

| Name of primer pair | Primer | | Base sequence | SEQ ID NO: |
|---|---|---|---|---|
| First primer pair | Forward | CT1P1F-2 | 5'-ccgctcattgacc agcaaataatc-3' | 5 |
| | Reverse | CT1P1R-9 | 5'-aagcttttttccgc atccaaacca-3' | 6 |
| Second primer pair | Forward | CT2F-4 | 5'-ccagaaaaagatag cgagcacaaagagag-3' | 7 |
| | Reverse | CT2_8 | 5'-cacagaattccgt cgatcataagg-3' | 10 |
| Primer pair for detecting *Neisseria gonorrhoea* | Forward | NG21F | 5'-attgtgttgaaac accgcccgg-3' | 15 |
| | Reverse | NG24R | 5'-ttcggctccttat tcggtttgacc-3' | 16 |

(2) Target Sequence
In the complete base sequence (GenBankID: HE603230.1) of the cryptic plasmid, a base sequence including a domain constituted with the 4,770$^{th}$ to 4,917$^{th}$ bases (148 base pairs: SEQ ID NO: 2) is a target sequence of the first primer pair according to the present invention.
In the complete base sequence (GenBankID: HE601796.2) of the CT genomic DNA, a base sequence including a domain constituted with the 782,264$^{th}$ to 782,436$^{th}$ bases (173 base pairs: SEQ ID NO: 3) is a target sequence of the second primer pair according to the present invention.

(3) Preparation of *Chlamydia* DNA

The *Chlamydia* DNA was used which was prepared in (3) of Example 1 and purified from each of the *Chlamydia* strains.

(4) Multiplex PCR

A 10 mM Tris-HCl buffer (pH 8.0) was prepared which contained primers (CT1P1F-2 and CT1P1R-9) each having a concentration of 0.8 µM, primers (CT2F-4 and CT2_8) each having a concentration of 0.4 µM, primers (NG21F and NG24R) each having a concentration of 0.15 µM, 1.2 mM $MgCl_2$, BSA at 100 µg/mL, 1% polyethylene glycol, 0.2% ProClin 300 (manufactured by Sigma-Aldrich Co. LLC.), dATP, dCTP, dGTP, and dTTP (manufactured by Toyobo Co., Ltd) each having a concentration of 0.25 mM, and KOD Exo(−) (manufactured by Toyobo Co., Ltd) at 60 units/mL, and the prepared buffer was used as a reaction solution for multiplex PCR.

Each of *Chlamydia* DNA prepared in (3) was suspended and added in an amount of 1 µL to 25 µL of the reaction solution for multiplex PCR, and the obtained resultant was used as a sample for multiplex PCR.

A 96-well plate (manufactured by Thermo Fisher Scientific Inc.) was filled with the sample for multiplex PCR, and by using a thermal cycler [StepOnePlus™ (manufactured by Thermo Fisher Scientific Inc.)], multiplex PCR was performed.

After heating the sample for 2 minutes at 95° C., 40 cycles were performed which each includes (1) heating the sample for 10 seconds at 97° C.→(2) heating the sample for 20 seconds at 65.5° C.→(3) heating the sample for 30 seconds at 71.5° C.

Then, by using a full automatic microchip-type capillary electrophoresis device 2100 Bioanalyzer (manufactured by Agilent Technologies), the obtained nucleic acid amplification product was subjected to capillary electrophoresis according to the protocol attached to the device. In this way, the obtained nucleic acid amplification product was separated and detected.

(5) Result

The results of the capillary electrophoresis are summarized in the following Table 11, In Table 11, "Positive" in the column of "Result" shows that at least either a target nucleic acid amplification product constituted with 148 base pairs or a target nucleic acid amplification product constituted with 173 base pairs was detected. "Negative" in the same column shows that a target nucleic acid amplification product in the complete base sequence of the cryptic plasmid and a target nucleic acid amplification product in the complete base sequence of the CT genomic DNA as a target were not detected.

TABLE 11

| Species | Strain | Result |
|---|---|---|
| C. caviae | GPIC | Negative |
| C. pneumoniae | KKpn | Negative |
|  | TW183 | Negative |
| C. pssitaci | cal10 | Negative |
|  | 6BC | Negative |
|  | Budgerigan-1 | Negative |
| C. trachomatis | A (Serovar) | Positive |
|  | B (Serovar) | Positive |
|  | Ba (Serovar) | Positive |
|  | C (Serovar) | Positive |
|  | D (Serovar) | Positive |
|  | E (Serovar) | Positive |
|  | F (Serovar) | Positive |
|  | G (Serovar) | Positive |

TABLE 11-continued

| Species | Strain | Result |
|---|---|---|
|  | H (Serovar) | Positive |
|  | I (Serovar) | Positive |
|  | J (Serovar) | Positive |
|  | K (Serovar) | Positive |
|  | L1 (Serovar) | Positive |
|  | L2 (Serovar) | Positive |
|  | L3 (Serovar) | Positive |

As is evident from the results shown in Table 11, only in a case here PCR was performed using the primer set, which contained the first primer pair according to the present invention and the second primer pair according to the present invention, and using DNA samples derived from the respective *Chlamydia trachomatis* strains as a template, a target nucleic acid amplification product was confirmed, and it is determined that these samples are positive for *Chlamydia trachomatis* could be made.

In contrast, in a case where multiplex PCR was performed in the same manner by using DNA samples derived from bacteria other than *Chlamydia trachomatis* as a template and using the primer set containing the first primer pair according to the present invention and the second primer pair according to the present invention, the corresponding target nucleic acid amplification product was not confirmed, and it is determined that these samples are negative for *Chlamydia trachomatis* could be made.

In addition, even though the primer pair for detecting *Neisseria gonorrhoeae* was present, by using the primer set containing the first primer pair according to the present invention and the second primer pair according to the present invention, *Chlamydia trachomatis* could be specifically detected.

From the above results, it was understood that *Chlamydia trachomatis* can be specifically detected using the primer set containing the first primer pair according to the present invention and the second primer pair according to the present invention.

Example 5 and Comparative Example 4 Influence of Human Genomic DNA on PCR Performed Using Various Primer Pairs (1) Primer Pair First primer pair according to the present invention The same primer pair as that in Example 1 was used.

Second primer pair (a) according to the present invention

The same primer pair as that in Example 4 was used.

Second primer pair (b) according to the present invention

A forward primer (CT2F-5) and a reverse primer (CT2_8) consisting of base sequences shown in the following Table 12 were used.

It should be noted that as the reverse primer (CT2_8), a primer in which the 5'-terminal of the sequence thereof was labeled with a fluorescent substance TAMRA was used.

Second primer pair (c) according to the present invention

A forward primer (CT2F-6) and a reverse primer (CT2_8) consisting of the base sequences shown in the following Table 12 were used.

It should be noted that as the reverse primer (CT2_8), a primer in which the 5'-terminal of the sequence thereof was labeled with a fluorescent substance TAMRA was used.

Primer pair of Patent Literature 1
The same primer pair as that in Comparative Example 1 was used.
Known primer pair targeted to CT genomic DNA
A forward primer (CT2_7) and a reverse primer (CT2_8) consisting of the base sequences shown in the following Table 12 were used.
It should be noted that as the reverse primer (CT2_8), a primer in which the 5'-terminal of the sequence thereof was labeled with a fluorescent substance TAMRA was used.
The forward primer (CT2_7) constituting a known primer pair targeted to CT genomic DNA is described in SeqID2 in U.S. Pat. No. 5,573,907. The reverse primer (CT2_8) is described in SeqID92 in WO93/00447.
Primer pair for detecting *Neisseria gonorrhoeae*
The same primer pair as that in Example 4 was used.
The primer pairs used are summarized in the following Table 12.

Reaction solution for multiplex PCR containing first primer pair according to the present invention, second primer pair (b) according to the present invention, and primer pair for detecting *Neisseria gonorrhoeae*
Reaction solution for multiplex PCR containing first primer pair according to the present invention, second primer pair (c) according to the present invention, and primer pair for detecting *Neisseria gonorrhoeae*
Reaction solution for multiplex PCR containing primer pair of Patent Literature 1, primer pair targeted to CT genomic DNA, and primer pair for detecting *Neisseria gonorrhoeae*

The human genomic DNA prepared in (2) was suspended and added in an amount of 1 μL to 25 μL of the four kinds of reaction solutions for multiplex PCR, and the obtained resultant was used as a sample for multiplex PCR.
By using the sample for multiplex PCR, multiplex PCR and capillary electrophoresis were performed by the same

TABLE 12

| | Name of primer pair | Primer | | Base sequence | SEQ ID NO: |
|---|---|---|---|---|---|
| Example (5-1) | First primer pair | Forward | CT1P1F-2 | 5'-ccgctcaaggaccagcaaataatc-3' | 5 |
| | | Reverse | CT1P1R-9 | 5'-aagcttttccgcatccaaacca-3' | 6 |
| | Second primer pair (a) | Forward | CT2F-4 | 5'-ccagaaaaagatagcgagcacaaagagag-3' | 7 |
| | | Reverse | CT2_8 | 5'-cacagaattccgtcgatcataagg-3' | 10 |
| | Primer pair for detecting *Neisseria gonorrhoea* | Forward | NG21F | 5'-attgtgttgaaacaccgcccgg-3' | 15 |
| | | Reverse | NG24R | 5'-ttcggctccttattcggtttgacc-3' | 16 |
| Example (5-2) | First primer pair | Forward | CT1P1F-2 | 5'-ccgctcaaggaccagcaaataatc-3' | 5 |
| | | Reverse | CT1P1R-9 | 5'-aagcttttccgcatccaaacca-3' | 6 |
| | Second primer pair (b) | Forward | CT2F-5 | 5'-ccagaaaaagatagcgagcacaaagaga-3' | 8 |
| | | Reverse | CT2_8 | 5'-cacagaattccgtcgatcataagg-3' | 10 |
| | Primer pair for detecting *Neisseria gonorrhoea* | Forward | NG21F | 5'-attgtgttgaaacaccgcccgg-3' | 15 |
| | | Reverse | NG24R | 5'-ttcggctccttattcggtttgacc-3' | 16 |
| Example (5-3) | First primer pair | Forward | CT1P1F-2 | 5'-ccgctcaaggaccagcaaataatc-3' | 5 |
| | | Reverse | CT1P1F-9 | 5'-aagcttttccgcatccaaacca-3' | 6 |
| | Second primer pair (c) | Forward | CT2F-6 | 5'-gccagaaaaagatagcgagcacaaagag-3' | 9 |
| | | Reverse | CT2_8 | 5'-cacagaattccgtcgatcataagg-3' | 10 |
| | Primer pair for detecting *Neisseria gonorrhoea* | Forward | NG21F | 5'-attgtgttgaaacaccgcccgg-3' | 15 |
| | | Reverse | NG24R | 5'-ttcggctccttattcggtttgacc-3' | 16 |
| Comparative Example 4 | Primer pair of Patent Literature 1 | Forward | IshikFw | 5'-cgctcaaggaccagcaaata-3' | 11 |
| | | Reverse | IshikRv | 5'-gcttttccgcatccaaac-3' | 12 |
| | Primer pair targeted to CT genomic DNA | Forward | CT2_7 | 5'-gatagcgagcacaaagagagctaa-3' | 17 |
| | | Reverse | CT2_8 | 5'-cacagaattccgtcgatcataagg-3' | 10 |
| | Primer pair for detecting *Neisseria gonorrhoea* | Forward | NG21F | 5'-attgtgttgaaacaccgcccgg-3' | 15 |
| | | Reverse | NG24R | 5'-ttcggctccttattcggtttgacc-3' | 16 |

Figure 3:
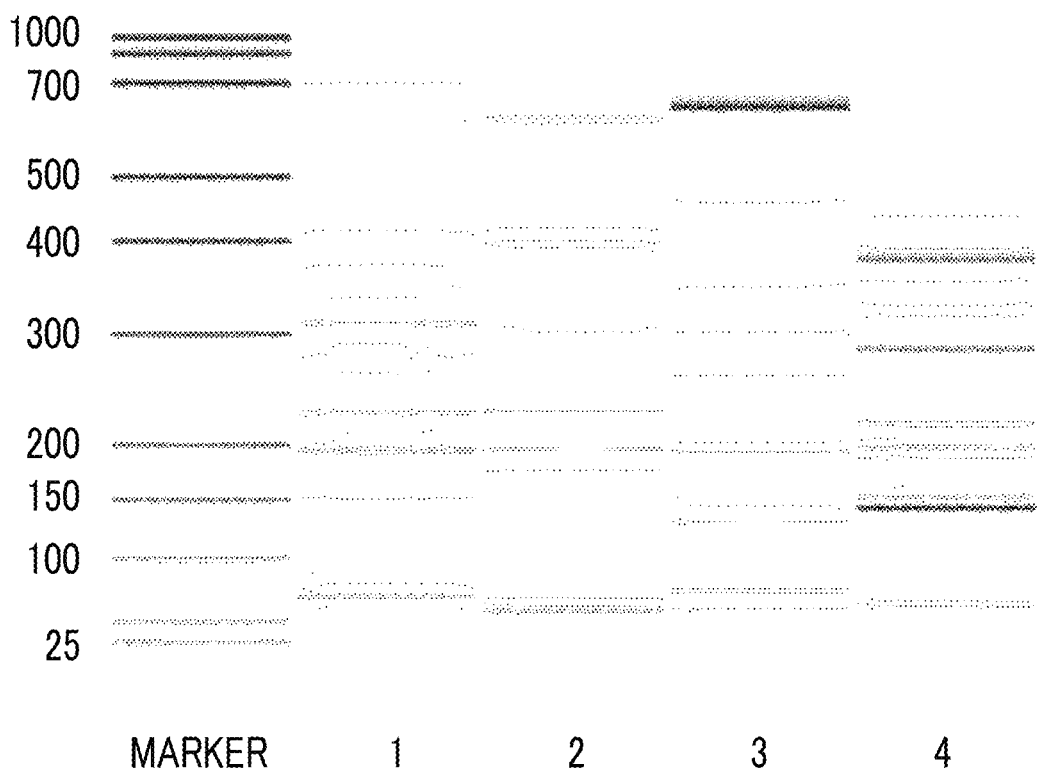
FIG. 3 is a phoretic diagram obtained by separating and detecting multiplex PCR amplification products, which are obtained in Example 5 and Comparative Example 4 from human genomic DNA-containing samples by using various primer pairs, by capillary electrophoresis.

(2) Preparation of Human Genomic DNA
Human genomic DNA prepared in (2) of Example 2 was used.
(3) Multiplex PCR
The following reaction solutions for multiplex PCR were prepared by the same method as that in (4) of Example 4, except that the primer pairs in (1) were used.
Reaction solution for multiplex PCR containing first primer pair according to the present invention, second primer pair (a) according to the present invention, and primer pair for detecting *Neisseria gonorrhoeae* method as that in (4) of Example 4, thereby separating and detecting nucleic acid amplification products.
(4) Result
FIG. 3 shows the results of the capillary electrophoresis. The primer pair used in each lane in FIG. 3 is shown in the following Table 13.
In FIG. 3, a band shows that a nucleic acid amplification product was detected. It should be noted that because the sample for multiplex PCR does not contain *Chlamydia trachomatis* DNA, in a case where a band showing a nucleic acid amplification product is detected, the band shows that the nucleic acid is nonspecifically amplified (nonspecific nucleic acid amplification product is obtained).

TABLE 13

| | Lane | Name of primer pair | | Primer | SEQ ID NO: |
|---|---|---|---|---|---|
| Example (5-1) | 1 | First primer pair | Forward | CT1P1F-2 | 5 |
| | | | Reverse | CT1P1R-9 | 6 |
| | | Second primer pair (a) | Forward | CT2F-4 | 7 |
| | | | Reverse | CT2_8 | 10 |
| | | Primer pair for detecting Neisseria gonorrhoea | Forward | NG21F | 15 |
| | | | Reverse | NG24R | 16 |
| Example (5-2) | 2 | First primer pair | Forward | CT1P1F-2 | 5 |
| | | | Reverse | CT1P1R-9 | 6 |
| | | Second primer pair (b) | Forward | CT2F-5 | 8 |
| | | | Reverse | CT2_8 | 10 |
| | | Primer pair for detecting Neisseria gonorrhoea | Forward | NG21F | 15 |
| | | | Reverse | NG24R | 16 |
| Example (5-3) | 3 | First primer pair | Forward | CT1P1F-2 | 5 |
| | | | Reverse | CT1P1R-9 | 6 |
| | | Second primer pair (c) | Forward | CT2F-6 | 9 |
| | | | Reverse | CT2_8 | 10 |
| | | Primer pair for detecting Neisseria gonorrhoea | Forward | NG21F | 15 |
| | | | Reverse | NG24R | 16 |
| Comparative Example 4 | 4 | Primer pair of Patent Literature 1 | Forward | IshikFw | 11 |
| | | | Reverse | IshikRv | 12 |
| | | Primer pair targeted to CT genomic DNA | Forward | CT2_7 | 17 |
| | | | Reverse | CT2_8 | 10 |
| | | Primer pair for detecting Neisseria gonorrhoea | Forward | NG21F | 15 |
| | | | Reverse | NG24R | 16 |

As is evident from the results shown in FIG. 3, in a case where the multiplex PCR was performed using the primer set containing the primer pair of Patent Literature 1 and the primer pair targeted to the CT genomic DNA (lane 4: Comparative Example 4), a large number of bands with high fluorescence intensity (thick bands) showing the nonspecific amplification of a nucleic acid were detected.

Particularly, it was understood that because the nucleic acid amplification product (band) between 140 base pairs and 200 base pairs has high fluorescence intensity and is close to 145 base pairs constituting the target sequence of the cryptic plasmid and to 164 base pairs constituting the target sequence of the CT genomic DNA, a false positive is highly likely to occur.

In contrast, in a case where the multiplex PCR was performed using the primer set containing the first primer pair according to the present invention and the second primer pair (a) according to the present invention (lane 1: Example 5-1), in a case where the multiplex PCR was performed using the primer set containing the first primer pair according to the present invention and the second primer pair (b) according to the present invention (lane 2: Example 5-2), and in a case where the multiplex PCR was performed using the primer set containing the first primer pair according to the present invention and the second primer pair (c) according to the present invention (lane 3: Example 5-3), even in the presence of the human genomic DNA, the number of bands showing the nonspecific amplification of a nucleic acid was small, and the fluorescence intensity of the bands was low (the bands were thin).

In addition, it was understood that because no band was confirmed at around 148 base pairs constituting the target sequence of the cryptic plasmid, 173 base pairs constituting the target sequence of the CT genomic DNA, and 174 base pairs, a false positive is hardly likely to occur.

From the above results, it was understood that in a case where the primer set containing the first primer pair according to the present invention and the second primer pair according to the present invention is used, the nonspecific amplification of a nucleic acid is suppressed, and a false positive is hardly likely to occur.

In contrast, it was understood that in a case where the primer set containing the primer pair of Patent Literature 1 and the primer pair targeted to the CT genomic DNA is used, the nonspecific amplification of a nucleic acid is not suppressed, and a false positive is highly likely to occur.

Example 6 and Comparative Example 5 Detection of Chlamydia trachomatis in Presence of Human Genomic DNA (1) Primer Pair
First primer pair according to the present invention
The same primer pair as that in Example 1 was used.
Second primer pair (a) according to the present invention
The same primer pair as that in Example 4 was used.
Second primer pair (b) according to the present invention
The same primer pair as that in Example 5 was used.
Primer pair of Patent Literature 1
The same primer pair as that in Comparative Example 1 was used.
Primer pair targeted to CT genomic DNA
The same primer pair as that in Comparative Example 4 was used.
Primer pair for detecting Neisseria gonorrhoeae
The same primer pair as that in Example 4 was used.
The primer pairs used are summarized in the following Table 14.

TABLE 14

| | Name of primer pair | | Primer | Base sequence | SEQ ID NO: |
|---|---|---|---|---|---|
| Example (6-1) | First primer pair | Forward | CT1P1F-2 | 5'-ccgctcaaggaccagcaaataatc-3' | 5 |
| | | Reverse | CT1P1R-9 | 5'-aagcttttccgcatccaaacca-3' | 6 |
| | Second primer pair (a) | Forward | CT2F-4 | 5'-ccagaaaaagatagcgagcacaaagagag-3' | 7 |
| | | Reverse | CT2_8 | 5'-cacagaattccgtcgatcataagg-3' | 10 |
| | Primer pair for detecting Neisseria gonorrhoea | Forward | NG21F | 5'-attgtgttgaaacaccgcccgg-3' | 15 |
| | | Reverse | NG24R | 5'-ttcggctccttattcggtttgacc-3' | 16 |
| Example (6-2) | First primer pair | Forward | CT1P1F-2 | 5'-ccgctcaaggaccagcaaataatc-3' | 5 |
| | | Reverse | CT1P1R-9 | 5'-aagcttttccgcatccaaacca-3' | 6 |
| | Second primer pair (b) | Forward | CT2F-5 | 5'-ccagaaaaagatagcgagcacaaagaga-3' | 8 |
| | | Reverse | CT2_8 | 5'-cacagaattccgtcgatcataagg-3' | 10 |
| | Primer pair | Forward | NG21F | 5'-attgtgttgaaacaccgcccgg-3' | 15 |

TABLE 14 -continued

| Name of primer pair | | Primer | Base sequence | SEQ ID NO: |
|---|---|---|---|---|
| | for detecting Neisseria gonorrhoea | Reverse NG24R | 5'-ttcggctccttattcggtttgacc-3' | 16 |
| Comparative Example 5 | Primer pair of Patent Literature 1 | Forward IshikFw<br>Reverse IshikRv | 5'-cgctcaaggaccagcaaata-3'<br>5'-gcttttccgcatccaaac-3' | 11<br>12 |
| | Primer pair targeted to CT genomic DNA | Forward CT2_7<br>Reverse CT2_8 | 5'-gatagcgagcacaaagagagctaa-3'<br>5'-cacagaattccgtcgatcataagg-3' | 17<br>10 |
| | Primer pair for detecting Neisseria gonorrhoea | Forward NG21F<br>Reverse NG24R | 5'-attgtgttgaaacaccgcccgg-3'<br>5'-ttcggctccttattcggtttgacc-3' | 15<br>16 |

(2) Target Sequence

In the complete base sequence (GenBankID: HE603230.1) of the cryptic plasmid, a base sequence including a domain (148 base pairs: SEQ ID NO: 2) constituted with the 4,770$^{th}$ to 4,917$^{th}$ bases is a target sequence of the first primer pair according to the present invention.

In the complete base sequence (GenBankID: HE601796.2) of the CT genomic DNA, a base sequence including a domain (173 base pairs: SEQ ID NO: 3) constituted with the 782,264$^{th}$ to 782,436$^{th}$ bases is a target sequence of the second primer pair (a) according to the present invention.

In the complete base sequence (GenBankID: HE601796.2) of the CT genomic DNA, a base sequence including a domain (173 base pairs: SEQ ID NO: 3) constituted with the 782,264$^{th}$ to 782,436$^{th}$ bases is a target sequence of the second primer pair (b) according to the present invention.

In the complete base sequence (GenBankID: HE603230.1) of the cryptic plasmid, a base sequence including a domain (145 base pairs: SEQ ID NO: 19) constituted with the 4,771$^{st}$ to 4,915$^{th}$ bases is a target sequence of the primer pair of Patent Literature 1.

In the complete base sequence (GenBankID: HE601796.2) of the CT genomic DNA, a base sequence including a domain (164 base pairs: SEQ ID NO: 20) constituted with the 782,264$^{th}$ to 782,427$^{th}$ bases is a target sequence of the primer pair targeted to the CT genomic DNA.

(3) Preparation of *Chlamydia* DNA

The *Chlamydia* DNA was used which was prepared in of Example 1 was used and purified from the *C. trachomatis* strain (D).

(4) Preparation of Human Genomic DNA

The human genomic DNA prepared in (2) of Example 2 was used.

(5) Multiplex PCR

The following reaction solutions for multiplex PCR were prepared by the same method as that in (4) of Example 4, except that the primer pairs in (1) were selected.

Reaction solution for multiplex PCR containing first primer pair according to the present invention, second primer pair (a) according to the present invention, and primer pair for detecting *Neisseria gonorrhoeae*

Reaction solution for multiplex PCR containing first primer pair according to the present invention, second primer pair (b) according to the present invention, and primer pair for detecting *Neisseria gonorrhoeae*

Reaction solution for multiplex PCR containing primer pair of Patent Literature 1, primer pair targeted to CT genomic DNA, and primer pair for detecting *Neisseria gonorrhoeae*

Each of the *Chlamydia* DNA and the human genomic DNA prepared as above was suspended and added in an amount of 1 μL to 25 μL of each of the three kinds of reaction solutions for multiplex PCR, and the obtained resultant was used as a sample for multiplex PCR.

By using the sample for multiplex PCR, multiplex PCR and capillary electrophoresis were performed by the same method as that in (4) of Example 4, thereby separating and detecting nucleic acid amplification products.

Furthermore, from the obtained fluorescence intensity (thickness) of the band of the target sequence of the cryptic plasmid, the nucleic acid concentration in the amplified cryptic plasmid was calculated.

(6) Result

Figure 4:
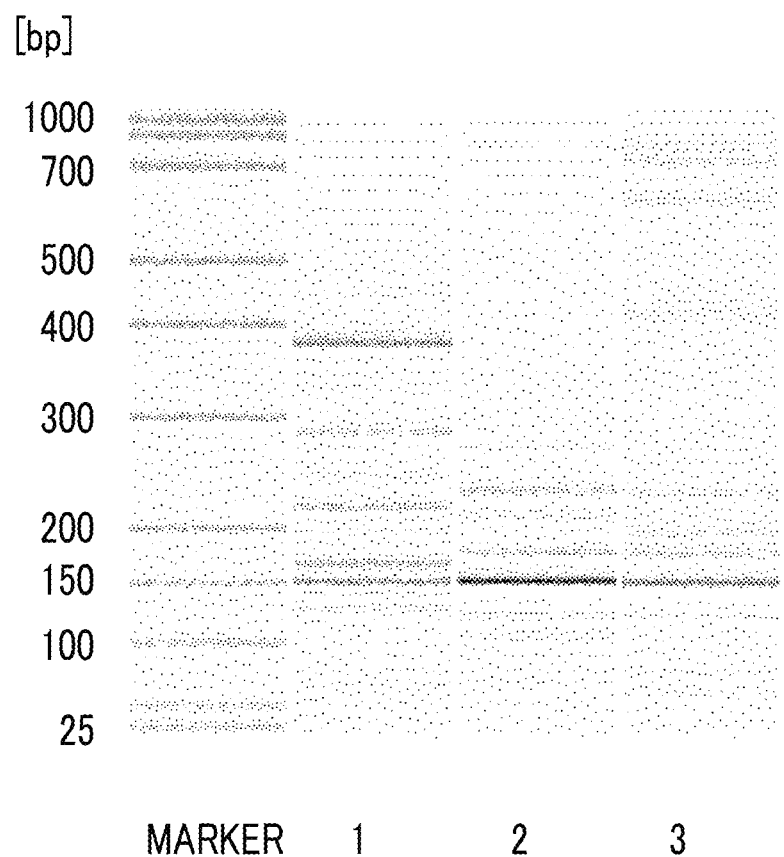
FIG. 4 is a phoretic diagram obtained by separating and detecting multiplex PCR amplification products, which are obtained in Example 6 and Comparative Example 5 from samples containing *Chlamydia trachomatis* DNA and human genomic DNA by using various primer pairs, by capillary electrophoresis.
Figure 5:
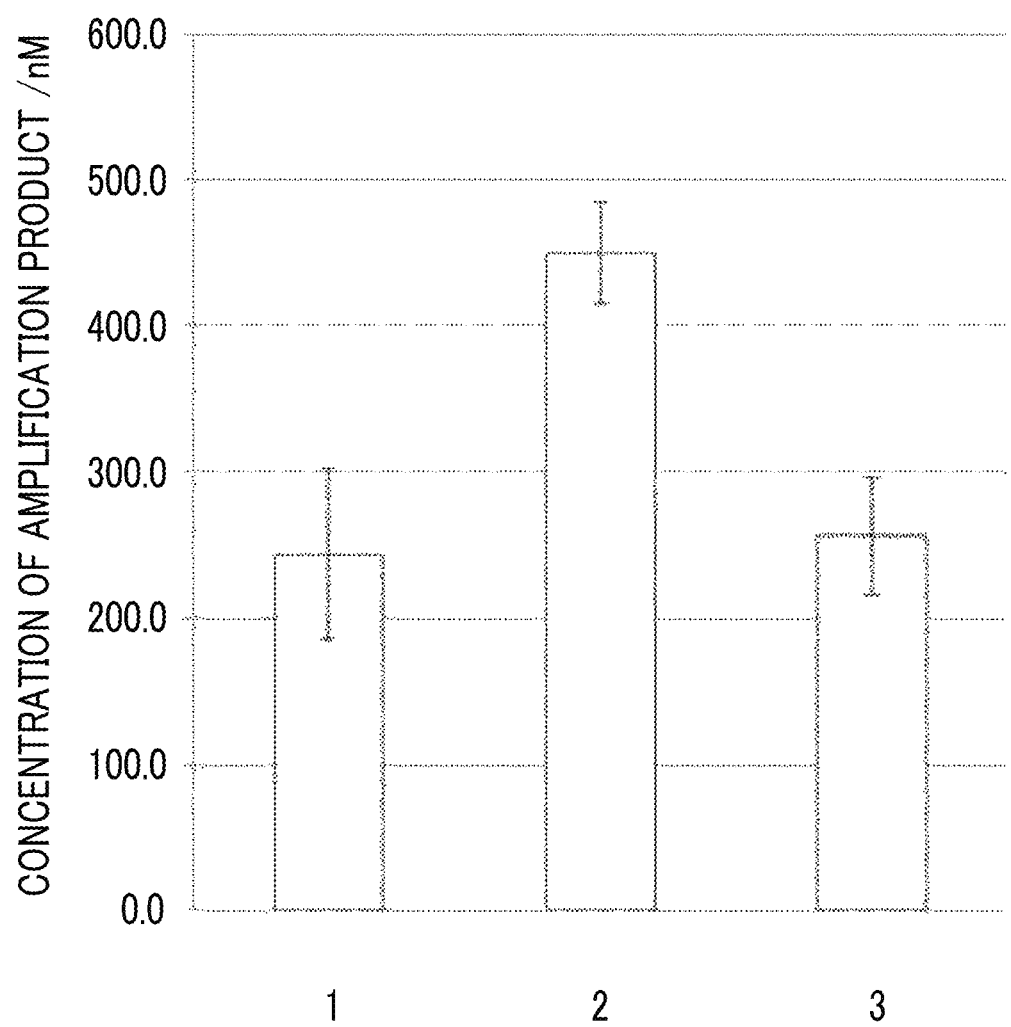
FIG. 5 is a view showing a nucleic acid concentration of a *Chlamydia trachomatis* cryptic plasmid that is calculated from fluorescence intensity (thickness) of a band corresponding to the *Chlamydia trachomatis* cryptic plasmid in the phoretic diagram obtained in Example 6 and Comparative Example 5.

FIGS. 4 and 5 show the results of the capillary electrophoresis. The primer pairs used in the lanes in FIGS. 4 and 5 are shown in the following Table 15.

In addition, in FIG. 4, a band shows that the nucleic acid was amplified.

It should be noted that in a case where the primer set containing the first primer pair according to the present invention and the second primer pair (a) according to the present invention is used (Example 6-1), and in a case where the primer set containing the first primer pair according to the present invention and the second primer pair (b) according to the present invention is used (Example 6-2), provided that a band is detected either at around 148 base pairs or at around 173 base pairs, because the target sequences are constituted with 148 base pairs and 173 base pairs respectively, it can be said that *Chlamydia trachomatis* as a target could be detected.

In a case where the primer set containing the primer pair of Patent Literature 1 and the primer pair targeted to the CT genomic DNA is used (Comparative Example 5), and a band is detected either at around 145 base pairs or at around 164 base pairs, because the target sequences are constituted with 145 base pairs and 164 base pairs respectively, it can be said that *Chlamydia trachomatis* as a target could be detected.

In addition, FIG. 5 is a diagram obtained by calculating the nucleic acid concentration from the fluorescence intensity (thickness) of the band of the target sequence of the cryptic plasmid in FIG. 4 and graphing the calculated concentration.

TABLE 15

| Lane | Name of primer pair | | Primer | SEQ ID NO: |
|---|---|---|---|---|
| Comparative Example 5 | 1 | Primer pair of Patent Literature 1 | Forward IshikFw | 11 |
| | | | Reverse IshikRv | 12 |
| | | Primer pair targeted to CT genomic DNA | Forward CT2_7 | 17 |
| | | | Reverse CT2_8 | 10 |
| | | Primer pair for detecting Neisseria gonorrhoea | Forward NG21F | 15 |
| | | | Reverse NG24R | 16 |
| Example (6-1) | 2 | First primer pair | Forward CT1P1F-2 | 5 |
| | | | Reverse CT1P1R-9 | 6 |
| | | Second primer pair (a) | Forward CT2F-4 | 7 |
| | | | Reverse CT2_8 | 10 |
| | | Primer pair for detecting Neisseria gonorrhoea | Forward NG21F | 15 |
| | | | Reverse NG24R | 16 |
| Example (6-2) | 3 | First primer pair | Forward CT1P1F-2 | 5 |
| | | | Reverse CT1P1R-9 | 6 |
| | | Second primer pair (b) | Forward C12F-5 | 8 |
| | | | Reverse CT2_8 | 10 |
| | | Primer pair for detecting Neisseria gonorrhoea | Forward NG21F | 15 |
| | | | Reverse NG24R | 16 |

As is evident from the results shown in FIG. 4, in a case where the multiplex PCR was performed using the primer set containing the primer pair of Patent Literature 1 and the primer pair targeted to the CT genomic DNA (lane 1: Comparative Example 5), bands were detected at around 145 base pairs and 164 base pairs, and *Chlamydia trachomatis* could be detected. However, at around 130 to 400 base pairs, a large number of bands with high fluorescence intensity (thick bands) showing the nonspecific amplification of a nucleic acid were confirmed.

Particularly, it vas understood that the nucleic acid amplification products (bands) between 130 base pairs and 200 base pairs have high fluorescence intensity and are close to 145 base pairs constituting the target sequence of the cryptic plasmid and to 164 base pairs constituting the target sequence of the CT genomic DNA, a false positive is highly likely to occur.

In contrast, in a case where the multiplex PCR was performed using the primer set containing the first primer pair according to the present invention and the second primer pair (a) according to the present invention (lane 2: Example 6-1) and in a case where the multiplex PCR was performed using the primer set containing the first primer pair according to the present invention and the second primer pair (b) according to the present invention (lane 3: Example 6-2), bands were detected at around 148 base pairs and 173 base pairs, and *Chlamydia trachomatis* could be detected.

In addition, the number of bands showing the nonspecific amplification of a nucleic acid was small, and the fluorescence intensity of the bands was low (the bands were thin).

In addition, as is evident from the results shown in FIG. 5, it was understood that between a case where the multiplex PCR was performed using the primer set containing the first primer pair according to the present invention and the second primer pair (a) according to the present invention (lane 2: Example 6-1) and a case where the multiplex PCR was performed using the primer set containing the first primer pair according to the present invention and the second primer pair (b) according to the present invention (lane 3: Example 6-2), particularly in the case where the multiplex PCR was performed using the primer set containing the first primer pair according to the present invention and the second primer pair (a) according to the present invention, the nucleic acid concentration of the target sequence of the cryptic plasmid was higher than in a case where the multiplex PCR was performed using the primer set containing the primer pair of Patent Literature 1 and the primer pair targeted to the CT genomic DNA (lane 1: Comparative Example 5).

From the above results, it was understood that in a case where the primer set containing the first primer pair according to the present invention and the second primer pair according to the present invention is used, the nonspecific amplification of a nucleic acid can be suppressed, and hence a false positive is hardly likely to occur. In addition, it was understood that because *Chlamydia trachomatis* can be detected with high sensitivity, a false negative is hardly likely to occur.

In contrast, it was understood that in a case where the primer set containing the primer pair of Patent Literature 1 and the primer pair targeted to the CT genomic DNA is used, the nonspecific amplification of a nucleic acid cannot be suppressed, and hence a false positive is highly likely to occur. In addition, it was understood that because *Chlamydia trachomatis* cannot be detected with high sensitivity, a false negative is very highly likely to occur.

INDUSTRIAL APPLICABILITY

According to the method for detecting *Chlamydia trachomatis* using the primer set of the present invention, even in a case where samples derived from wine, the pharynx, and the cervix that are highly likely to contain human genomic DNA are used, it is possible to reduce misdiagnoses in making a diagnosis and to specifically detect *Chlamydia trachomatis* with higher sensitivity and accuracy compared to a case where the method of the related art is used.

The invention claimed is:

1. A primer set for detecting *Chlamydia trachomatis* comprising:
   a first primer pair composed of a combination of a forward primer consisting of a base sequence represented by SEQ ID NO: 5 and a reverse primer consisting of a base sequence represented by SEQ ID NO: 6,
   wherein at least one of the primers of the first primer pair is labeled with a labeling substance selected from a fluorescent substance, a radioisotope, an enzyme, and a luminescent substance.

2. The primer set according to claim 1, further comprising:
   a second primer pair composed of a combination of a forward primer comprising a base sequence represented by any of SEQ ID NOS: 7 to 9 and a reverse primer comprising a base sequence represented by SEQ ID NO: 10.

3. The primer set according to claim 2, wherein the second primer pair is composed of a combination of a forward primer comprising a base sequence represented by SEQ ID NO: 7 and a reverse primer comprising a base sequence represented by SEQ ID NO: 10.

4. The primer set according to claim 2, wherein at least one of the primers of the second primer pair is labeled with a labeling substance.

5. The primer set according to claim 4, wherein the labeling substance for at least one of the primers of the second primer pair is selected from a fluorescent substance, a radioisotope, an enzyme, and a luminescent substance.

6. A method for detecting *Chlamydia trachomatis* comprising:
   performing a nucleic acid amplification reaction by using a primer set comprising a first primer pair composed of a forward primer consisting of a base sequence represented by SEQ ID NO: 5 and a reverse primer consisting of a base sequence represented by SEQ ID NO: 6 and using a nucleic acid in a sample as a template; and
   detecting a nucleic acid amplification product obtained.

7. A method for detecting *Chlamydia trachomatis* comprising:
   (1) performing a nucleic acid amplification reaction by using a primer set comprising a first primer pair composed of a combination of a forward primer consisting of a base sequence represented by SEQ ID NO: 5 and a reverse primer consisting of a base sequence represented by SEQ ID NO: 6 and using a nucleic acid in a sample as a template; and
   (2) performing electrophoresis for a nucleic acid amplification product obtained by the nucleic acid amplification reaction of (1) and determining a presence or absence of *Chlamydia trachomatis* based on a result of the electrophoresis.

8. The method according to claim 6, wherein the nucleic acid amplification reaction is PCR.

9. The method according to claim 7, wherein the electrophoresis is capillary electrophoresis.

10. A reagent kit for detecting *Chlamydia trachomatis*, comprising the primer set according to claim 1.

11. The reagent kit according to claim 10, wherein the primer set further comprises a second primer pair composed of a combination of a forward primer comprising a base sequence represented by any of SEQ ID NOS: 7 to 9 and a reverse primer comprising a base sequence represented by SEQ ID NO: 10.

12. The reagent kit according to claim 11, wherein the second primer pair is composed of a combination of a forward primer comprising a base sequence represented by SEQ ID NO: 7 and a reverse primer comprising a base sequence represented by SEQ ID NO: 10.

13. The reagent kit according to claim 12, wherein at least one of the primers of the second primer pair is labeled with a labeling substance.

14. The method according to claim 6, wherein the primer set further comprises a second primer pair composed of a combination of a forward primer comprising a base sequence represented by any of SEQ ID NOs: 7 to 9 and a reverse primer comprising a base sequence represented by SEQ ID NO: 10.

15. The method according to claim 7, wherein the primer set further comprises a second primer pair composed of a combination of a forward primer comprising a base sequence represented by any of SEQ ID NOs: 7 to 9 and a reverse primer comprising a base sequence represented by SEQ ID NO: 10.

16. The method according to claim 14, wherein the second primer pair is composed of a combination of a forward primer comprising a base sequence represented by SEQ ID NO: 7 and a reverse primer pair comprising a base sequence represented by SEQ ID NO: 10.

17. The method according to claim 15, wherein the second primer pair is composed of a combination of a forward primer comprising a base sequence represented by SEQ ID NO: 7 and a reverse primer comprising a base sequence represented by SEQ ID NO: 10.

18. The method according to claim 14, wherein at least one of the primers is labeled with a labeling substance.

19. The method according to claim 15, wherein at least one of the primers is labeled with a labeling substance.

20. The method according to claim 6, wherein at least one of the primers is labeled with a labeling substance.

21. The method according to claim 7, wherein at least one of the primers is labeled with a labeling substance.

* * * * *